US008409575B2

(12) United States Patent
Lannfelt et al.

(10) Patent No.: US 8,409,575 B2
(45) Date of Patent: *Apr. 2, 2013

(54) ANTIBODIES SPECIFIC FOR AMYLOID BETA PROTOFIBRIL

(75) Inventors: Lars Lannfelt, Stockholm (SE); Camilla Nilsberth, Norrköping (SE); Anita Campbell, Höllviken (SE); Jan Näslund, Stockholm (SE)

(73) Assignee: BioArctic Neuroscience AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/218,592

(22) Filed: Aug. 26, 2011

(65) Prior Publication Data
US 2012/0027755 A1 Feb. 2, 2012

Related U.S. Application Data

(62) Division of application No. 12/051,785, filed on Mar. 19, 2008, now abandoned, which is a division of application No. 11/654,508, filed on Jan. 18, 2007, now Pat. No. 7,700,719, which is a division of application No. 09/899,815, filed on Jul. 9, 2001, now Pat. No. 7,179, 463.

(60) Provisional application No. 60/217,098, filed on Jul. 10, 2000.

(30) Foreign Application Priority Data

Jul. 7, 2000 (EP) .................................. 00202387

(51) Int. Cl.
*A61K 39/395* (2006.01)
*C07K 16/28* (2006.01)

(52) U.S. Cl. ................ 424/133.1; 530/388.22; 514/17.8
(58) Field of Classification Search .......................... None
See application file for complete search history.

(56) References Cited

U.S. PATENT DOCUMENTS

| | | | |
|---|---|---|---|
| 5,231,000 A * | 7/1993 | Majocha et al. ............... 435/7.1 |
| 5,604,102 A | 2/1997 | McConlogue et al. |
| 5,612,486 A | 3/1997 | McConlogue et al. |
| 5,679,531 A | 10/1997 | König et al. |
| 5,753,624 A | 5/1998 | McMichael et al. |
| 5,817,626 A | 10/1998 | Findeis et al. |
| 5,850,003 A | 12/1998 | McLonlogue et al. |
| 5,851,996 A | 12/1998 | Kline |
| 5,854,204 A | 12/1998 | Findeis et al. |
| 5,854,215 A | 12/1998 | Findeis et al. |
| 5,985,242 A | 11/1999 | Findeis et al. |
| 6,054,114 A | 4/2000 | Lansbury, Jr. et al. |
| 6,114,133 A | 9/2000 | Seubert et al. |
| 6,174,916 B1 | 1/2001 | McMichael |
| 6,218,506 B1 | 4/2001 | Krafft et al. |
| 6,245,964 B1 | 6/2001 | McLonlogue et al. |
| 6,303,567 B1 | 10/2001 | Findeis et al. |
| 6,319,498 B1 | 11/2001 | Findeis et al. |
| 7,179,463 B2 | 2/2007 | Lannfelt et al. |
| 7,427,392 B1 | 9/2008 | Seubert et al. |
| 7,700,719 B2 | 4/2010 | Lannfelt et al. |
| 8,025,878 B2 | 9/2011 | Gellerfors et al. |
| 8,106,164 B2 | 1/2012 | Gellerfors et al. |
| 2002/0162129 A1 | 10/2002 | Lannfelt et al. |
| 2003/0068316 A1 | 4/2003 | Klein et al. |
| 2003/0187011 A1 | 10/2003 | Lashuel et al. |
| 2003/0232758 A1 | 12/2003 | St. George-Hyslop et al. |
| 2004/0049134 A1 | 3/2004 | Tosaya et al. ................ 601/2 |
| 2004/0170641 A1 | 9/2004 | Schenk |
| 2004/0171815 A1 | 9/2004 | Schenk et al. |
| 2004/0171816 A1 | 9/2004 | Schenk et al. |
| 2005/0031629 A1 | 2/2005 | Schenk |
| 2005/0124016 A1 | 6/2005 | LaDu et al. |
| 2005/0142132 A1 | 6/2005 | Schenk et al. |
| 2005/0191314 A1 | 9/2005 | Schenk |
| 2005/0249725 A1 | 11/2005 | Schenk et al. |
| 2006/0079447 A1 | 4/2006 | Wetzel |
| 2006/0166275 A1 | 7/2006 | Krafft et al. |
| 2006/0178302 A1 | 8/2006 | Krafft et al. |
| 2006/0193850 A1 | 8/2006 | Warne et al. |
| 2006/0228349 A1 | 10/2006 | Acton et al. |
| 2006/0240486 A1 | 10/2006 | Johnson-Wood et al. |
| 2006/0280733 A1 | 12/2006 | Kayed et al. |

(Continued)

FOREIGN PATENT DOCUMENTS

| | | |
|---|---|---|
| EP | 0 783 104 | 7/1997 |
| WO | WO 91/16819 | 11/1991 |

(Continued)

OTHER PUBLICATIONS

International Preliminary Examination Report for International Application No. PCT/SE01/01553, completed Oct. 23, 2002 submitted Jan. 30, 2002.
Communication pursuant to Rules 109 and 110 EPC in European Patent Application No. 01945896.7, dated Mar. 5, 2003.
Reply to Communication pursuant to Rules 109 and 110 EPC in European Patent Application No. 01945896.7, dated Apr. 1, 2003.
Communication pursuant to Article 96(2) EPC issued in European Patent Application No. 01945896.7, dated Sep. 30, 2005.
Reply to Communication under Art. 96(2) in European Patent Application No. 01945896.7, dated Apr. 7, 2006.
Communication pursuant to Article 96(2) EPC issued in European Patent Application No. 01945896.7, dated May 22, 2006.
Reply to Communication under Art. 96(2) in European Patent Application No. 01945896.7, dated Sep. 22, 2006.
Communication pursuant to Article 96(2) EPC issued in European Patent Application No. 01945896.7, dated Apr. 24, 2007.
Reply to Communication under Art. 96(2) in European Patent Application No. 01945896.7, dated Nov. 5, 2007.

(Continued)

*Primary Examiner* — Olga N Chernyshev
(74) *Attorney, Agent, or Firm* — Clark & Elbing LLP

(57) ABSTRACT

The invention relates to a purified antibody or fragment thereof that specifically binds an Aβ protofibril. The invention further relates to a composition that includes such antibodies. The invention also relates to using such antibodies and compositions for treating a patient having of suspected of having Alzheimer's disease.

12 Claims, 2 Drawing Sheets

U.S. PATENT DOCUMENTS

Figure 1:
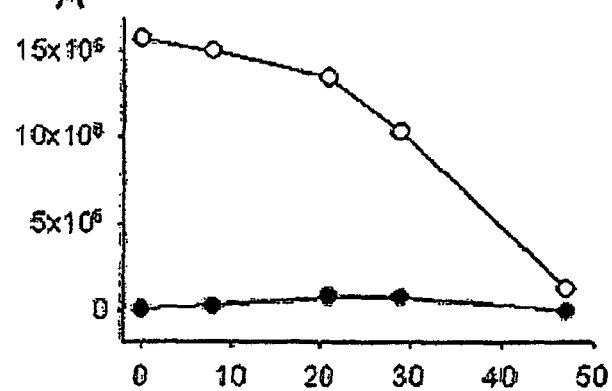
Figure 1:
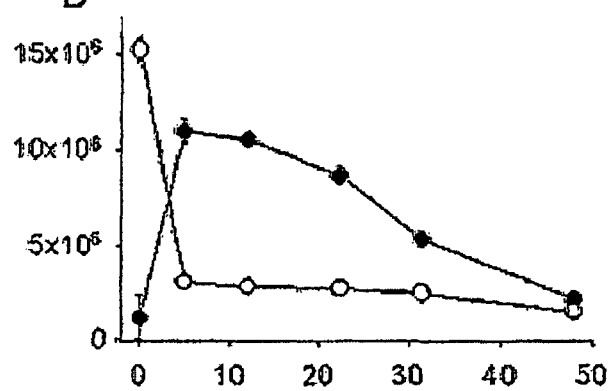
Figure 1:
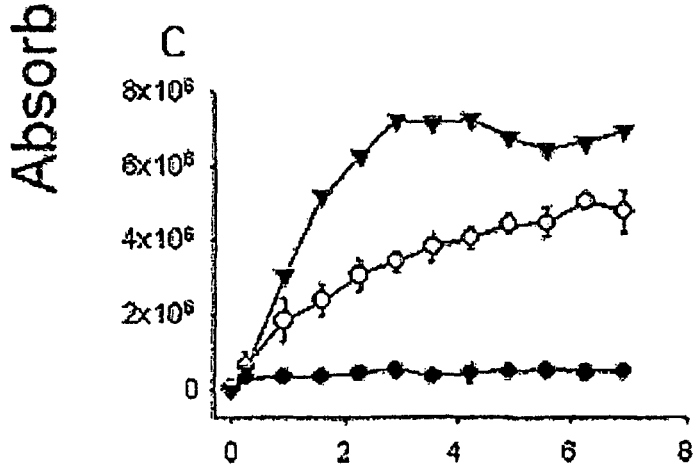

| | | | |
|---|---|---|---|
| 2007/0048312 | A1 | 3/2007 | Klein et al. |
| 2007/0081998 | A1 | 4/2007 | Kinney et al. |
| 2007/0098721 | A1 | 5/2007 | Hillen et al. |
| 2007/0099185 | A1 | 5/2007 | Hagen et al. |
| 2007/0110750 | A1 | 5/2007 | Glabe et al. |
| 2007/0148167 | A1 | 6/2007 | Strohl |
| 2008/0181902 | A1 | 7/2008 | Lannfelt et al. |

FOREIGN PATENT DOCUMENTS

| | | |
|---|---|---|
| WO | 9511994 | 5/1995 |
| WO | WO 95/11994 | 5/1995 |
| WO | 9531996 | 11/1995 |
| WO | WO 95/31996 | 11/1995 |
| WO | WO 96/15452 A1 | 5/1996 |
| WO | WO 97/41856 | 11/1997 |
| WO | WO 98/33815 | 8/1998 |
| WO | 9927944 | 6/1999 |
| WO | WO 99/27944 | 6/1999 |
| WO | WO 99/27944 A1 | 6/1999 |
| WO | WO 99/27949 | 6/1999 |
| WO | 0039310 | 7/2000 |
| WO | WO 00/39310 | 7/2000 |
| WO | WO 00/71671 | 11/2000 |
| WO | 0072876 | 12/2000 |
| WO | WO 00/72870 | 12/2000 |
| WO | WO 00/72876 | 12/2000 |
| WO | WO 00/72880 | 12/2000 |
| WO | WO 01/10900 | 2/2001 |
| WO | 01/39796 | 6/2001 |
| WO | WO 01/39796 | 6/2001 |
| WO | WO 01/90182 | 11/2001 |
| WO | WO 02/03911 A2 | 1/2002 |
| WO | WO 03/089460 | 10/2003 |
| WO | WO 03/104437 | 12/2003 |
| WO | WO 2004/024090 | 3/2004 |
| WO | WO 2004/031400 | 4/2004 |
| WO | WO 2005/019828 | 3/2005 |
| WO | WO 2005/019828 A1 | 3/2005 |
| WO | WO 2005/025516 | 3/2005 |
| WO | WO 2005/089539 A1 | 9/2005 |
| WO | WO 2005/123775 | 12/2005 |
| WO | WO 2005/123775 A1 | 12/2005 |
| WO | WO 2006/014478 | 2/2006 |
| WO | WO 2006/047254 | 5/2006 |
| WO | WO 2006/055178 | 5/2006 |
| WO | WO 2006/066233 | 6/2006 |
| WO | WO 2006/083533 | 8/2006 |
| WO | WO 2006/094724 | 9/2006 |
| WO | WO 2006/137354 | 12/2006 |
| WO | WO 2007/005358 | 1/2007 |
| WO | WO 2007/005359 | 1/2007 |
| WO | WO 2007/050359 | 5/2007 |
| WO | WO 2007/062088 | 5/2007 |
| WO | WO 2007/108756 | 9/2007 |
| WO | WO 2007/108756 A1 | 9/2007 |
| WO | WO 2009/133521 A2 | 11/2009 |

OTHER PUBLICATIONS

Summons to Attend Oral Proceedings Pursuant to Rule 115(1) EPC in European Patent Application No. 01945896.7, dated Jul. 25, 2008.
Reply to Summons to Attend Oral Proceedings Pursuant to Rule 115(1) EPC in European Patent Application No. 01945896.7, dated Oct. 10, 2008.
Consultation by Telephone with the Applicant/Representative in European Patent Application No. 01945896.7, dated Nov. 5, 2008.
Minutes of the Oral Proceedings before the Examining Division in European Patent Application No. 01945896.7, dated Dec. 17, 2008.
Decision to Refuse a European Patent Application issued in European Patent Application No. 01945896.7, dated Sep. 11, 2009.
Notice of Appeal filed in European Patent Application No. 01945896.7, dated Nov. 3, 2009.
Appellant's Statement of Grounds of Appeal filed in European Patent Application No. 01945896.7, dated Jan. 14, 2010.
Commencement of Proceedings before the Board of Appeal in European Patent Application No. 01945896.7, dated Feb. 4, 2010.
Restriction Requirement (U.S. Appl. No. 09/899,815; U.S. Patent No. 7,179,463), mailed Jul. 3, 2002.
Reply to Restriction Requirement (U.S. Appl. No. 09/899,815; U.S. Patent No. 7,179,463), filed Sep. 3, 2002.
Office Action (U.S. Appl. No. 09/899,815; U.S. Patent No. 7,179,463), mailed Nov. 19, 2002.
Reply to Office Action (U.S. Appl. No. 09/899,815; U.S. Patent No. 7,179,463), filed Apr. 21, 2003.
Office Action (U.S. Appl. No. 09/899,815; U.S. Patent No. 7,179,463), mailed Jun. 25, 2003.
Interview Summary (U.S. Appl. No. 09/899,815; U.S. Patent No. 7,179,463), dated Oct. 21, 2003.
Notice of Appeal (U.S. Appl. No. 09/899,815; U.S. Patent No. 7,179,463), filed Nov. 25, 2003.
Reply to Office Action (U.S. Appl. No. 09/899,815; U.S. Patent No. 7,179,463), filed Dec. 18, 2003.
Resubmission of Reply to Office Action (U.S. Appl. No. 09/899,815; U.S. Patent No. 7,179,463), filed Feb. 3, 2004.
Advisory Action (U.S. Appl. No. 09/899,815; U.S. Patent No. 7,179,463), mailed Feb. 20, 2004.
Request For Continued Examination (U.S. Appl. No. 09/899,815; U.S. Patent No. 7,179,463), filed Mar. 25, 2004.
Restriction Requirement (U.S. Appl. No. 09/899,815; U.S. Patent No. 7,179,463), mailed Jun. 10, 2004.
Reply to Restriction Requirement (U.S. Appl. No. 09/899,815; U.S. Patent No. 7,179,463), filed Sep. 10, 2004.
Supplemental Reply to Restriction Requirement (U.S. Appl. No. 09/899,815; U.S. Patent No. 7,179,463), filed Sep. 21, 2004.
Office Action (U.S. Appl. No. 09/899,815; U.S. Patent No. 7,179,463), mailed Nov. 24, 2004.
Reply to Office Action (U.S. Appl. No. 09/899,815; U.S. Patent No. 7,179,463), filed Mar. 24, 2005.
Notice of Non-Compliant Amendment (U.S. Appl. No. 09/899,815; U.S. Patent No. 7,179,463), mailed May 12, 2005.
Reply to Notice of Non-Compliant Amendment (U.S. Appl. No. 09/899,815; U.S. Patent No. 7,179,463), filed May 27, 2005.
Office Action (U.S. Appl. No. 09/899,815; U.S. Patent No. 7,179,463), mailed Jul. 7, 2005.
Reply to Office Action (U.S. Appl. No. 09/899,815; U.S. Patent No. 7,179,463), filed Oct. 7, 2005.
Office Action (U.S. Appl. No. 09/899,815; U.S. Patent No. 7,179,463), mailed Nov. 9, 2005.
Reply to Office Action (U.S. Appl. No. 09/899,815; U.S. Patent No. 7,179,463), filed Mar. 9, 2006.
Declaration Under Rule 132 (U.S. Appl. No. 09/899,815; U.S. Patent No. 7,179,463), filed Mar. 9, 2006.
Office Action (U.S. Appl. No. 09/899,815; U.S. Patent No. 7,179,463) mailed May 8, 2006.
Reply to Office Action (U.S. Appl. No. 09/899,815; U.S. Patent No. 7,179,463), filed Aug. 8, 2006.
Notice of Allowance (U.S. Appl. No. 09/899,815; U.S. Patent No. 7,179,463), mailed Oct. 16, 2006.
Response in connection to Communication pursuant to Article 94(3) EPC dated Mar. 22, 2012 as filed May 30, 2012.
Declaration of Anders Lindgren and Lars Lannfelt accompanying Response in connection to Communication pursuant to Article 94(3) EPC dated Mar. 22, 2012 as filed May 30, 2012.
Communication for European Patent Application No. 05753672.4, dated Mar. 22, 2012.
Communication for European Patent Application No. 05753672.4, dated Jul. 6, 2009.
Third Party Observations for European Patent Application No. 05753672.4, dated Jan. 16, 2012.
Response to Communication for European Patent Application No. 05753672.4, dated Jan. 17, 2011.
Response to Communication for European Patent Application No. 01945896.7, dated Apr. 7, 2006.
Declaration of Lars Lannfelt, dated Mar. 7, 2006.
Declaration of Lars Lannfelt, received by the EPO on Sep. 22, 2006.
Response to Communication for European Patent Application No. 01945896.7, dated Sep. 22, 2006.
Statement of Grounds for European Patent Application No. 01945896.7, dated Jan. 14, 2010.

Walsh et al. "Amyloid β-protein fibrillogenesis: Detection of a protofibrillar intermediate," *J. Biol. Chem.* 272:22364-22372 (1997).

Walsh et al. "Amyloid β-protein fibrillogenesis: Structure and biological activity of protofibrillar intermediates," *J. Biol. Chem.* 274:25945-25952 (1999).

Nichols et al., "Growth of β-Amyloid(1-40) Protofibrils by Monomer Elongation and Lateral Association. Characterization of Distinct Products by Light Scattering and Atomic Force Microscopy," *Biochemistry* 41(19):6115-6127, 2002.

*Cayman Chemical Catalog No. 321000*, CAS Registry No. 75899-68-2, Copyright Cayman Chemical Company, May 16, 2006.

*Cayman Chemical Catalog No. 321000*, CAS Registry No. 75899-68-2, Copyright Cayman Chemical Company, Apr. 12, 2009.

Bieschke et al., "Small Molecule Oxidation Products Trigger Disease-Associated Protein Misfolding," *Accounts of Chemical Research* 39:611-619, 2006.

Chartier-Harlin et al., "Alpha-Synuclein Locus Duplication as a Cause of Familial Parkinson's Disease," *The Lancet* 364:1167-1169, 2004.

Conway et al., "Acceleration of Oligomerization, not Fibrillization, is a Shared Property of Both α-Synuclein Mutations Linked to Early-Onset Parkinson's Disease: Implications for Pathogenesis and Therapy," *Proc Natl Acad Sci USA* 97: 571-576, 2000.

El-Agnaf et al., "Detection of Oligomeric Forms of α-Synuclein Protein in Human Plasma as a Potential Biomarker for Parkinson's Disease," *The FASEB Journal* 20:419-425, 2006.

Hansen et al., "The Lewy Body Variant of Alzheimer's Disease: a Clinical and Pathologic Entity," *Neurology* 40:1-8, 1990.

Jefferis, Roy, "Glycosylation as a Strategy to Improve Antibody-Based Therepeutics," *Nature Reviews Drug Discovery* 8:226-234, 2009.

Klucken et al., "Clinical and Biochemical Correlates of Insoluble α-Synuclein in Dementia with Lewy Bodies," *Acta Neuropathol* 111:101-108, 2006.

Krüger et al., "Ala30Pro Mutation in the Gene Encoding a α-Synuclein in Parkinson's Disease." *Nature Genetics* 18:106-108, 1998.

Näsström et al., "The Lipid Peroxidation Metabolite 4-Oxo-2-Nonenal Cross-Links α-Synuclein Causing Rapid Formation of Stable Oligomers," *Biochemical and Biophysical Research Communications* 378:872-876, 2009.

Polymeropoulos et al., "Mutation in the α-Synuclein Gene Identified in Families with Parkinson's Disease," *Science* 276:2045-2047, (1997).

Qin et al., "Effect of 4-Hydroxy-2-Nonenal Modification on α-Synuclein Aggregation," *Journal of Biological Chemistry* 282:5862-5870, 2007.

Shamoto-Nagai et al. "In Parkinsonian Substantia Nigra, α-Synuclein is Modified by Acrolein, a Lipid-Peroxidation Product, and Accumulates in the Dopamine Neurons with Inhibition of Proteasome Activity," *J Neural Transm* 114:1559-1567, 2007.

Singleton et al., "α-Synuclein Locus Triplication Causes Parkinson's Disease," *Science* 302:841, 2003.

Tsigelny et al., "Mechanisms of Hybrid Oligomer Formation in the Pathogenesis of Combined Alzheimer's and Parkinson's Diseases," *PLoS ONE* 3(9): e3135, 2008.

Yoritaka et al., "Immunohistochemical Detection of 4-Hydroxynonenal Protein Adducts in Parkinson Disease," *Proc. Natl. Acad. Sci. USA* 93:2696-2701, 1996.

Zarranz et al., "The New Mutation, E46K, of α-Synuclein Causes Parkinson and Lewy Body Dementia," *Annals of Neurology* 55:164-173, 2004.

Decision to Refuse European Patent Application 01 945 896.7-2402 dated Nov. 9, 2009.

Appellant's Statement of Grounds of Appeal together with Main Request, First Auxiliary Request, and Second Auxiliary Request, and Declaration by Professor Dominic Walsh dated Jan. 14, 2010.

Golabek et al., "The Interaction between Apolipoprotein E and Alzheimer's Amyloid β-Peptide Is Dependent on β-Peptide Conformation," *J. Biol. Chem.* 271(18):10602-10606, 1996.

Harper et al., "Assembly of Aβ Amyloid Protofibrils: An In Vitro Model for a Possible Early Event in Alzheimer's Disease," *Biochemistry* 38:8972-8980, 1999.

Kamino et al., "Linkage and Mutational Analysis of Familial Alzheimer Disease Kindreds for the APP Gene Region," *Am. J. Hum. Genet.* 51:998-1014, 1992.

Miravelle et al., "Substitutions at Codon 22 of Alzheimer's Aβ Peptide Induce Diverse Conformational Changes and Apoptotic Effects in Human Cerebral Endothelial Cells," *J. Biol. Chem.* 275:27110-27116, 2000.

Nilsberth et al., "A Novel APP Mutation (E693G)—The Arctic Mutation Causing Alzheimer's Disease with Vascular Symptoms," *Soc. Neurosci. Abstr.* 25:297; 1999.

Schenk et al., "Immunization with Amyloid-β Attenuates Alzheimer-Disease-Like Pathology in the PDAPP," *Nature* 400:173-177, 1999.

Soto et al., "The Conformation of Alzheimer's β Peptide Determines the Rate of Amyloid Formation and Its Resistance to Proteolysis," *Biochem. J.* 1:314:701-707, 1996.

Walsh et al., "Amyloid β-Protein Fibrillogenesis. Detection of a Protofibrillar Intermediate," *J. Biol. Chem.* 272(35):22364-22372, 1997.

Walsh et al., "Amyloid β-Protein Fibrillogenesis. Structure and Biological Activity of Protofibrillar Intermediates," *J. Biol. Chem.* 274(36):25945-25952, 1999.

Extended European Search Report for European Patent Application No. 08019830.2, May 21, 2010.

Klein et al., "Oligemia-Induced Expression of c-fos and Oxidative Stress-Related Protein in the Murine Brain," 30th Annual Meeting of the Society of Neuroscience, New Orleans, LA, Nov. 4-9, 2000, *Soc. Neurosci. Abstracts* 26(1-2), Abstract 383.15, 2000.

Klyubin et al., "Inhibitory Effect of Amyloid-β Peptide with the Arctic Mutation on Long-term Potentiation in Area CA1 of Rat Hippocampus In Vivo," *J. Physiol.,* 551P, C32, 2003.

Tagliavani et al., "A New βAPP Mutation Related to Hereditary Cerebral Haemorrhage," *Alz. Report* 2(Suppl. 1):S28, Abstract 23, 1999.

Communication from European Patent Application No. 05753672.4-2402, mailed Jul. 6, 2009.

Communication Pursuant to Article 94(3) EPC in European Application No. 05753672.4, dated Jul. 6, 2009.

Reply to Communication Pursuant to Article 94(3) EPC in European Application No. 05753672.4, dated Nov. 5, 2009.

Communication Pursuant to Article 94(3) EPC in European Application No. 05753672.4, dated Jul. 8, 2010.

Reply to Communication Pursuant to Article 94(3) EPC in European Application No. 05753672.4, dated Jan. 17, 2011.

Communication Pursuant to Rule 114(2) EPC (Observations by a Third Party) in European Application No. 05753672.4, dated Jan. 24, 2012.

Communication Pursuant to Article 94(3) EPC in European Application No. 05753672.4, dated Mar. 22, 2012.

Reply to Communication Pursuant to Article 94(3) EPC in European Application No. 05753672.4, dated May 30, 2012.

U.S. Appl. No. 09/369,236, filed Aug. 4, 1999, Krafft et al.
U.S. Appl. No. 09/745,057, filed Dec. 20, 2000, Krafft et al.
U.S. Appl. No. 10/166,856, filed Jun. 11, 2002, Klein et al.
U.S. Appl. No. 60/621,776, filed Oct. 25, 2004, Lambert et al.
U.S. Appl. No. 60/652,538, filed Feb. 14, 2005, Shughrue et al.
U.S. Appl. No. 60/217,098, filed Jul. 10, 2000, Lannfelt et al.
U.S. Appl. No. 11/570,995, filed Dec. 20, 2006, Gellerfors et al.
U.S. Appl. No. 12/294,207, filed Sep. 23, 2008, Gellerfors et al.

Axelman et al., "A Large Swedish Family with Alzheimer's Disease with a Codon 670/671 Amyloid Precursor Protein Mutation," *Arch. Neurol.* 51:1193-1197, 1994.

Forsell et al., "Amyloid Precursor Protein Mutation at Codon 713 (Ala →Val) Does Not Cause Schizophrenia: Non-Pathogenic Variant Found at Codon (Silent)," *Neurosci. Lett.* 184:90-93, 1995.

Jensen et al., "Quantification of Alzheimer Amyloid β Peptides Ending at Residues 40 and 42 by Novel ELISA Systems," *Mol. Med.* 6:291-302, 2000.

Johansson et al., "Physiochemical Characterization of the Alzheimer's Disease-Related Peptides Aβ1-42 Arctic and Aβ1-42 wt" *FEBS J.* 273:2618-2630, 2006.

Johnston et al., "Increased β-Amyloid Release and Levels of Amyloid Precursor Protein (APP) in Fibroblast Cell Lines From Family Members With the Swedish Alzheimer's Disease APP670/671 Mutation," *FEBS Lett.* 354:274-278, 1994.

Lannfelt et al., "Amyloid Precursor Protein Mutation Causes Alzheimer's Disease in a Swedish Family," *Neurosci. Lett.* 168:254-256, 1994.

Lannfelt et al., "Amyloid β-Peptide in Cerebrospinal Fluid in Individuals with the Swedish Alzheimer Amyloid Precursor Protein Mutation," *Neurosci. Lett.* 199:203-206, 1995.

Lannfelt et al., "Genetics of Alzheimer's Disease—Routes to the Pathophysiology," *J. Neural. Transm.* [Suppl.] 59:155-161, 2000.

Lannfelt et al., "Genetics, Pathophysiology and Aβ Protofibril Formation in Alzheimer's Disease," *Neurobiol. Aging* 25(Suppl. 2): Poster Session P2: Epidemiology and Risk Factors of Alzheimer's Disease p. 2-268; S308, 2004.

Lannfelt et al., "Monoclonal Antibodies Selective for Aβ Protofibrils Reduce Plaque Sensitive Detection of Alzheimer Aβ Protofibrils by Burden in Transgenic Mice Models of Alzheimer's Disease Conformation Specific ELISA," ICAD meeting, Uppsala University, Sweden, Jul. 16, 2006.

Lannfelt et al., "Monoclonal Antibodies Selective for Aβ Protofibrils: Detection of Protofibrils and Reduction of Plaque Burden in Tg-mice Models of Alzheimer's Disease," SfN meeting, Uppsala University, Sweden, Oct. 17, 2006.

Mullan et al., "A Pathogenic Mutation for Probable Alzheimer's Disease in the APP Gene at the N-terminus of β-Amyloid," *Nature Genet.* 1:345-347, 1992.

Nilsberth et al., "A Novel APP Mutation (E693G)—The Arctic Mutation, Causing, Alzheimer's Disease with Vascular Symptoms," *Society for Neuroscience Annual Meeting*, Miami Beach, Abstract, 120.4; Nov. 1999.

Nilsberth et al., "The 'Arctic' APP Mutation (E693G) Causes Alzheimer's Disease by Enhanced Aβ Protofibril Formation," *Neurobiology of Aging*, May-Jun. 2000, 21, Abstract 265, Supplement 1, 1-304.

Nilsberth et al., "The Artic APP Mutation (E693G) Causes Alzheimer's Disease Through a Novel Mechanism: Increased Amyloid β Protofibril Formation and Decreased Amyloid β Levels in Plasma and Conditioned Media," *Neurobiol. Aging* 21:S58, 2000.

Nilsberth et al., "The 'Arctic' APP Mutation (E693G) Causes Alzheimer's Disease by Enhanced Aβ Protofibril Formation," *Nature Neurosci.* 4(9):887-893, 2001.

Päiviö et al., "Unique Physicochemical Profile of β-Amyloid Peptide Variant Aβ1-40E22G Protofibrils: Conceivable Neuropathogen in Arctic Mutant Carriers," *J. Med. Biol.* 339:145-159, 2004.

Sahlin et al., "The Arctic Alzheimer Mutation Favors Intracellular Amyloid-β Production by Making Amyloid Precursor Protein Less Available to α-secretase," *J. Neurochem.* 101:854-862, 2007.

Scheuner et al., "Secreted Amyloid β-Protein Similar to That in the Senile Plaques of Alzheimer's Disease is Increased In Vivo by the Presenilin 1 and 2 and APP Mutations Linked to Familial Alzheimer's Disease," *Nature Med.* 2(8):864-870, 1996.

Stenh et al., "Amyloid-β Oligomers are Inefficiently Measured by Enzyme-Linked Immunosorbent Assay," *Ann. Neurol.* 58: 147-150, 2005.

Stenh et al., "The Arctic Mutation Interferes with Processing of the Amyloid Precursor Protein," *NeuroReport* 13: 1857-1860, 2002.

Minutes from Oral Proceedings for European Patent Application No. 01945896.7-2402, dated Dec. 17, 2008.

European Examination Report (EP 01 945 896.7), dated Apr. 24, 2007.

European Examination Report (EP 01 945 896.7), dated May 22, 2006.

European Examination Report (EP 01 945 896.7), dated Sep. 30, 2005.

Extended European Search Report from European Patent Application No. 07747965.7, dated May 13, 2009.

International Preliminary Report (PCT/US2003/30930), completed Feb. 6, 2006.

International Preliminary Report on Patentability (PCT/US2003/19640), completed Aug. 7, 2006.

International Preliminary Report on Patentability (PCT/SE01/01553), completed Oct. 23, 2002.

International Preliminary Report on Patentability (PCT/SE05/000993), issued Dec. 28, 2006.

International Preliminary Report on Patentability (PCT/SE07/000292), issued Sep. 23, 2008.

International Search Report (PCT/SE01/01553), mailed Feb. 4, 2002.

International Search Report (PCT/SE05/000993), mailed Oct. 4, 2005.

International Search Report (PCT/SE07/000292), mailed Jul. 20, 2007.

Notice of intent to grant a European patent and Annex (Reasons for Decision) (EP 01 945 896.7), dated Mar. 18, 2009.

Reply to Examination Report (European Patent Application No. 01945896.7-2402), mailed Apr. 7, 2006.

Reply to Examination Report (European Patent Application No. 01945896.7-2402), mailed Sep. 22, 2006.

Reply to Examination Report (European Patent Application No. 01945896.7-2402), mailed Nov. 5, 2007.

Request Pursuant to Oral Proceedings (European Patent Application No. 01945896.7-2402), mailed Oct. 10, 2008.

Summons to Attend Oral Proceedings (European Patent Application No. 01945896.7-2402), dated Jul. 25, 2008.

Written Opinion of the International Searching Authority (PCT/SE05/000993), mailed Oct. 4, 2005.

Written Opinion of the International Searching Authority (PCT/SE07/000292), mailed Jul. 20, 2007.

Declaration of Pär Gellerfors, dated Nov. 28, 2010.

Giasson et al., "A Panel of Epitope-Specific Antibodies Detects Protein Domains Distributed Throughout Human Alpha-Synuclein in Lewy Bodies of Parkinson's Disease," *J. Neurosci. Res.* 59:528-533, 2000.

Johnston et al., "Increased β-Amyloid Release and Levels of Amyloid Precursor Protein (APP) in Fibroblast Cell Lines from Family Members with the Swedish Alzheimer's Disease APP670/671," *FEBS Letters* 354:274-278, 1994.

Lannfelt et al., "Amyloid Precursor Protein Mutation Causes Alzheimer's Disease in a Swedish Family," *Neurosci. Letters* 168:254-256, 1994.

Lannfelt et al., "Amyloid β-Peptide in Cerebrospinal Fluid in Individuals with the Swedish Alzheimer Amyloid Precursor Protein Mutation," *Neurosci. Letters* 199:203-206 (1995).

Citron, et al. Nature Med 3, 67-72 (1997).
Conway, et al., Proc Natl Acad Sci USA 97, 571-576 (2000).
Dalfó et al., J. Neuro. 64:816-830, (2005).
De Jonghe, et al., *Neurobiol Disease* 5, 281-286 (1998).
Forsell, et al, *Neurosci Lett* 184, 90-93 (1995).
Giulian et al., J Biol Chem, 273, 29719-19726, (1998).
Grabowski et al., *Ann Neurol* 49, 697-705 (2001).
Hardy, Trends Neurosci. 20, 154-159 (1997).
Harper et al., *Biochemistry* 38, 8972-8980 (1999).
Hendriks, et al., *Nature Genet* 1, 218-221 (1992).
Kamino, et al., Am J Hum Genet 51, 998-1014 (1992).
Levy, et al., *Science* 248, 1124-1126 (1990).
Mullan, et al., Nature Genet 1, 345-347 (1992).
Palmert et al. PNAS 86:6338 (1989).
Qin et al., Journ. Bio. Chem. 282, 8:5862-5870, (2007).
Schenk et al., *Nature*, 400, 173-177 (1999).
Scheuner, et al., Nature Med 2, 864-869 (1996).
Serpell L.C. *Biochim. Biophys.Acta*, 1502, 16-30 (2000).
Sherrington et al. *Nature* 375:754 (1995).
St. George-Hyslop et al. *Science* 235:885 (1987).
Suzuki, et al., Science 264, 1336-1340 (1994).
Tagliavini, et al., *Alz Report* 2, S28 (1999).
Walsh et al., J Biol Chem 272, 22364-22372 (1997).
Walsh et al., J Biol Chem 36, 25945-25952 (1999).
Weidemann et al. *Cell* 57:115 (1989).
Wirak et al. *Science* 253:323 (1991).
Yoritaka et al., Proc. Natl. Acad. 93:2696-2701, (1996).
Vickers, 2002, Drugs Aging, 19(7), pp. 487-494.

Schenk, et al., Immunization with amyloid-β attenuates Alzheimer-disease-like pathology in the PDAPP, Letters to Nature, 400:173-177 (Jul. 8, 1999).
St. George-Hyslop, et al., Genetic linkage studies suggest that Alzheimer's disease is not a single homogeneous disorder, Letters to Nature, 347:194-197 (Sep. 13, 1990).
Wirak, et al., Deposits of Amyloid β Protein in the Central Nervous System of Transgenic Mice, Science, 253:323-325 (Jul. 19, 1991).
St. George-Hyslop, et al., The Genetic Defect Causing Familial Alzheimer's Disease Maps on Chromosome 21, Science, 235:885-890( Feb. 20, 1987).
Walsh, et al., Amyloid β-Protein Fibrillogenesis, the Journal of Biological Chemistry, 272(35):22364-22372 (Aug. 29, 1997).
Weidemann, et al., Identification, Biogenesis, and Localization of Precursors of Alzheimer's Disease A4 Amyloid Protein, Cell 57:115-126 (Apr. 7, 1989).
Giulian, et al., The HHQK Domain of β-Amyloid Provides a Structural Basis for the Immunopathology of Alzheimer's Disease, The Journal of Biological Chemistry, 273(45):29719-29726 (Nov. 6, 1998).
Sherrington et al., Cloning of agene bearing missense mutations in early-onset familial Alzheimer's disease, Nature, 375:754-760 (Jun. 29, 1995).
Palmert, et al., The β-amyloid protein precursor of Alzheimer disease has soluble derivatives found in human brain and cerebrospinal fluid, Proc. Natl. Acad. Sci. USA, 86:6338-6342 (Aug. 1989).
Levy, et al., Mutation of the Alzheimer's Disease Amyloid Gene in Hereditary Cerebral Hemorrhage, Dutch Type, Science, 248:1124-1126 (Jun. 1, 1990).
Suzuki, et al., An Increase Percentage of Long Amyloid β Protein Secreted by Familial Amyloid β Protein Precursor ($\beta APP_{717}$) Mutants, Science, 264:1336-1340 (May 27, 1994).
Conway, et al. Acceleration of oligomerization, not fibrillization, is a shared property of both α-synuclein mutations linked to early-onset Parkinson's disease: Implications for pathogenesis and therapy, PNAS, 97(2):571-576 (Jan. 18, 2000).
Mullan, et al., A pathogenic mutation for probable Alzheimer's disease in the APP gene at the N-terminus of β-amyloid, Natue Genetics, 1:345-347 (Aug. 1992).
Hendriks, et al., Presenile dementia and cerebral haemorrhage linked to a mutation at codon 692 of the β-amyloid precursor protein gene, Nature Genetics, 1:218-221 (Jun. 1992).
De Jonghe et al., Flemish and Dutch Mutations in Amyloid β Precursor Protein Hane Different Effects on Amyloid β Secretion, Neurobiology of Disease, 5:281-286 (accepted for publ. Aug. 19, 1998.
Kamino, et al., Linkage and Mutational Analysis of Familial Alzheimer Disease Kindreds for the APP Gene Regin, Am. J. Hum. Genet. 51:998-1014 (revision reveived Jyly 24, 1992.
Citron, et al., Mutant presenilins of ALzheinmer's disease increase production of 42-residue amyloid β-protein in both transfected cells and transgenic mice, Nature Medicin, 3(1):67-72 (Jan. 1997).
Forsell, et al., Amyloid precursor protein mutation at codon 713(Ala-Val) does not cause schizophrenia: non-pathogenic variant found at codon 705 (silent), Newroscience Letters, 184:90-93 (accepted Nov. 18, 1994).
Hardy, Amyloid, the presenillins and Alzheimer's disease, Trends Neurosci., 20(4):154-159 (1997).
Grabowski, et al., Novel Amyloid Precursor Protein Mutation in an Iowa Family with Dementia and Severe Cerebral Amyloid Angiopathy, Ann. Neurol., 49:697-705 (published online Mar. 19, 2001).
Scheuner, et al., Secreted amyloid β-protein similar to that in thesenile plaques of Alzheimer's disease is increased in vivo by the presenilin 1 and 2 and APP mutations linked to familial Alzheimer's disease, Nature Medicine, 2(8):864-870 (Aug. 1996).
Serpell, Alzheimer's amyloid fibrils: structure and assembly, Biochimica et Biophysica Acta, 1502:16-30 (accepted Nov. 24, 1999).
Harper, et al., Assembly of Aβ Amyloid Protofibrils: An in Vitro Model for aPossible Early Event in Alzheimer's Disease, Biochemistry, 38:8972-8980 (published online Jun. 18, 1999).

Bacskai, et al., Imaging of amyloid-β deposits in brains of living mice permits direct observation of clearance of plaques with immunotherapy, Nature Medicine, 7(3):369-372 (Mar. 2001).
Frenkel, et al., Immunization against Alzheimer's β-amyloid plaques via EFRH phage administration, PNAS, 97(21):11455-11459 (Oct. 10, 2000).
Bard, et al., Peripherally administered antibodies against amyloid β-peptide enter the central nervous system and reduce pathology in a mouse model of Alzheimer disease, Nature Medicine, 6(8):916-919 (Aug. 2000).
Morgan, et al., Aβ peptide vaccination prevents memory loss in an animal model of Alzheimer's disease, Nature, 408:982-985 (Dec. 2000).
Janus, et al., Aβ peptide immunization reduces behavioural impairment and plaques in a model of Alzheimer's disease, Nature, 408:979-982 (Dec. 2000).
Chen, et al., A learning deficit related to age and β-amyloid plaques in a mouse model of Alzheimer's disease, Nature, 408:975-978 (Dec. 2000).
Andreasen and Blennow, "Beta-amyloid (Abeta) Protein in Cerebrospinal Fluid as a Biomarker for Alzheimer's Disease," *Peptides* 23:1205-1214, 2002.
Bacskai et al., "Imaging of Amyloid-β Deposits in Brains of Living Mice Permits Direct Observation of Clearance of Plaques with Immunotherapy," *Nature Med.* 7(3):369-372, 2001.
Bard et al., "Peripherally Administered Antibodies Against Amyloid β-Peptide Enter the Central Nervous System and Reduce Pathology in a Mouse Model of Alzheimer Disease," *Nature Med.* 6(8):916-919, 2000.
Barghorn et al., "Globular Amyloid β-Peptide Oligomer: A Homogenous and Stable Neuropathological Protein in Alzheimer's Disease," *J. Neurochem.* 95:834-47, 2005.
Bayer et al., "Evaluation of the Safety and Immunogenicity of Synthetic Aβ42 (AN1792) in Patients with AD," *Neurology* 64:94-101, 2005.
Bitan et al., "Amyloid β-Protein (Aβ) Assembly: Aβ40 and Aβ42 Oligomerize Through Distinct Pathways," *Proc. Natl. Acad. Sci. U.S.A.* 100:330-5, 2003.
Blanchard et al., "Efficient Reversal of Alzheimer's Disease Fibril Formation and Elimination of Neurotoxicity by a Small Molecule," *Proc. Natl. Acad. Sci. U.S.A.* 101(40):14326-32, 2004.
Cai et al., "Release of Excess Amyloid β-Protein from a Mutant Amyloid β-Protein Precursor," *Science* 259:514-516, 1993.
Caughey and Lansbury, "Protofibrils, Pores, Fibils, and Neurodegeneration: Separating the Responsible Protein Aggregates from the Innocent Bystanders," *Ann. Rev. Neurosci.* 26:267-98, 2003.
Chen et al., "A Learning Deficit Related to Age and β-Amyloid Plaques in a Mouse Model of Alzheimer's Disease," *Nature* 408:975-978, 2000.
Chromy et al., "Self-Assembly of $A\beta_{1-42}$ Into Globular Neurotoxins," *Biochemistry* 42:12749-12760, 2003.
Chromy et al., "Stability of Small Oligomers of $A\beta_{1-42}$(ADDLs)," *Society for Neuroscience* 25:2129; 852.5, 1999.
Citron et al., "Mutation of the β-Amyloid Precursor Protein in Familial Alzheimer's Disease Increases β-Protein Production," *Nature* 360:672-674, 1992.
Citron et al., "Mutant Presenilins of Alzheimer's Disease Increase Production of 42-Residue Amyloid β-Protein in Both Transfected Cells and Transgenic Mice," *Nature Med.* 3(1):67-72, 1997.
Conway et al., "Acceleration of Oligomerization, Not Fibrillization, is a Shared Property of Both α-Synuclein Mutations Linked to Early-Onset Parkinson's Disease: Implications for Pathogenesis and Therapy," *Proc. Natl. Acad. Sci. U.S.A.* 97(2):571-576, 2000.
Dahlgren et al., "Oligomeric and Fibrillar Species of Amyloid-β Peptides Differentially Affect Neuronal Viability," *J. Biol. Chem.* 277:32046-53, 2002.
Dalfo et al., "Evidence of Oxidative Stress in the Neocortex in Incidental Lewy Body Disease," *J. Neuropathol. Exp. Neurol.* 64(9):816-830, 2005.
De Jonghe et al., "Flemish and Dutch Mutations in Amyloid β Precursor Protein Have Different Effects on Amyloid β Secretion," *Neurobiol. Dis.* 5:281-286, 1998.

DeMarco et al., "From Conversion to Aggregation: Protofibril Formation of the Prion Protein," *Proc. Natl. Acad. Sci. U.S.A.* 101:2293-2298, 2004.

Dodart et al., "Immunization Reverses Memory Deficits Without Reducing Brain Aβ Burden in Alzheimer's Disease Model," *Nature Neurosci.* 5:452-457, 2002.

El-Agnaf et al., "Oligomerization and Toxicity of β-Amyloid-42 Implicated in Alzheimer's Disease," *Biochem. Biophys. Res. Comm.* 273:1003-1007, 2000.

Enya et al., "Appearance of Sodium Dodecyl Sulfate-Stable Amyloid β-Protein (Aβ) Dimer in the Cortex During Aging," *Am. J. Pathol.* 154:271-279, 1999.

Finder and Glockshuber, "Amyloid-β Aggregation," *Neurodegener. Dis.* 4(1):13-27, 2007.

Frackowiak et al., "Non-Fibrillar β-Amyloid Protein is Associated with Smooth Muscle Cells of Vessel Walls in Alzheimer Disease," *J. Neuropathol. Exp. Neurol.* 53:637-645, 1994.

Frenkel et al, "Modulation of Alzheimer's Beta-amyloid Neurotoxicity by Site-directed Single-chain Antibody," *Neuroimmunomodulation* 6:444, 1999.

Frenkel et al., "Immunization Against Alzheimer's β-Amyloid Plaques Via EFRH Phage Administration," *Proc. Natl. Acad. Sci. U.S.A.* 97(21):11455-11459, 2000.

Frenkel et al, "Modulation of Alzheimer's Beta-amyloid Neurotoxicity by Site-directed Single-chain Antibody," *J. Neuroimmunol.* 106:23-31, 2000.

Giulian et al., "The HHQK Domain of β-Amyloid Provides a Structural Basis for the Immunopathology of Alzheimer's Disease," *J. Biol. Chem.* 273(45):29719-29726, 1998.

Glenner et al., "Alzheimer's Disease: Initial Report of the Purification and Characterization of a Novel Cerebrovascular Amyloid Protein," *Biochem. Biophys. Res. Comm.* 120(3):885-890, 1984.

Grabowski et al., "Novel Amyloid Precursor Protein Mutation in an Iowa Family with Dementia and Severe Cerebral Amyloid Angiopathy," *Ann. Neurol.* 49:697-705, 2001.

Guerette et al., "Oligomeric Aβ in PBS-Soluble Extracts of Human Alzheimer Brain," *Society for Neuroscience* 25:2129; 852.1, 1999.

Hardy, "Framing β-Amyloid," *Nature Genet.* 1:233-234, 1992.

Hardy, "Amyloid, the Presenilins and Alzheimer's Disease," *Trends Neurosci.* 20(4):154-159, 1997.

Harper et al., "Observation of Metastable Aβ Amyloid Protofibrils by Atomic Force Microscopy," *Chem. Biol.* 4:119-125, 1997.

Hartley et al., "Protofibrillar Intermediates of Amyloid β-Protein Induce Acute Electrophysiological Changes and Progressive Neurotoxicity in Cortical Neurons," *J. Neurosci.* 19(20):8876-8884, 1999.

Hendriks et al., "Presenile Dementia and Cerebral Hemorrhage Linked to a Mutation at Codon 692 of the β-Amyloid Precursor Protein Gene," *Nature Genet.* 1:218-221, 1992.

Hock and Nitsch, "Clinical Observations with AN-1792 Using TAPIR Analyses," *Neurodegener Dis.* 2:273-276, 2005.

Hoshi et al., "Spherical Aggregates of β-Amyloid (Amylospheroid) Show High Neurotoxicity and Activate Tau Protein Kinase I/glycogen Synthase Kinase-3β," *Proc. Natl. Acad. Sci. U.S.A.* 100(11):6370-6375, 2003.

Isaacs et al., "Acceleration of Amyloid β-Peptide Aggregation by Physiological Concentrations of Calcium," *J. Biol. Chem.* 281(38):27916-23, 2006.

Janus et al., "A β Peptide Immunization Reduces Behavioral Impairment and Plaques in a Model of Alzheimer's Disease," *Nature* 408:979-982, 2000.

Kang et al., "The Precursor of Alzheimer's Disease Amyloid A4 Protein Resembles a Cell-surface Receptor," *Nature* 325:733-736, 1987.

Kayed et al., "Immunization With a Molecular Mimic of a Toxic Aggregates Generates a Conformation-Dependent Antibody Specific for High Molecular Weight A Aggregates (Micelles and Protofibrils)," 32nd Annual Meeting of the Society for Neuroscience, Orlando, Florida (*Society for Neuroscience Abstract Viewer and Itinerary Planner*, Abstract No. 685.3, 2002).

Kayed et al., "Common Structure of Soluble Amyloid Oligomers Implies Common Mechanism of Pathogenesis," *Science* 300:486-489, 2003.

Kirkitadze et al., "Paradigm Shifts in Alzheimer's Disease and Other Neurodegenerative Disorders: The Emerging Role of Oligomeric Assemblies," *J. Neurosci. Res.* 1, 69:567-77, 2002.

Klafki et al., "Therapeutic Approaches to Alzheimer's Disease," *Brain* 129:2840-2855, 2006.

Klein et al., "Oligomer/Conformation-Dependent Aβ Antibodies," *Soc. Neurosci. Abstr.* Presentation No. 475.11, Tuesday Nov. 7, 2000.

Klein et al., "Targeting Small Aβ Oligomers: The Solution to an Alzheimer's Disease Conundrum?" *Trends Neurosci.* 24:219-224, 2001.

Klein, "Aβ Toxicity in Alzheimer's Disease," *Contemporary Clinical Neuroscience: Molecular Mechanisms of Neurodegenerative Diseases* 1.1 Introduction, 2001.

Klyubin et al., "Soluble Arctic Amyloid β Protein Inhibits Hippocampal Long-Term Potentiation In Vivo," *Eur. J. Neurosci.* 19:2839-2846, 2004.

Kuo et al., "Water-soluble Aβ (N-40, N-42) Oligomers in Normal and Alzheimer Disease Brains," *J. Biol. Chem.* 271:4077-4081, 1996.

Lambert et al., "Diffusible, Nonfibrillar Ligands Derived From Aβ$_{1-42}$ Are Potent Central Nervous System Neurotoxins," *Proc. Natl. Acad. Sci. U.S.A.* 95:6448-6453, 1998.

Lambert et al., "Neuron Dysfunction and Death Caused by Small Aβ Oligomers: Role of Signal Transduction," *Society for Neuroscience* 25:2129, 1999.

Lambert et al., "Vaccination With Soluble Aβ Oligomers Generates Toxicity-Neutralizing Antibodies," *J. Neurochem.* 79:595-605, 2001.

Lambert et al., "Monoclonal Antibodies that Target Pathological Assemblies of Aβ," *J. Neurochem.* 100:23-35, 2007.

Lashuel et al., "Mixtures of Wild-Type and a Pathogenic (E22G) Form of Aβ40 In Vitro Accumulate Protofibrils, Including Amyloid Pores," *J. Mol. Biol.* 332:795-808, 2003.

Lee et al., "Targeting Amyloid-β Peptide (Aβ) Oligomers by Passive Immunization with a Conformation-selective Monoclonal Antibody Improves Learning and Memory in Aβ Precursor Protein (APP) Transgenic Mice," *J. Biol. Chem.* 2006 281 :4292-4299.

Levy et al., "Mutation of the Alzheimer's Disease Amyloid Gene in Hereditary Cerebral Hemorrhage, Dutch Type," *Science* 248:1124-1126, 1990.

Liu et al., "Residues 17-20 and 30-35 of β-Amyloid Play Critical Roles in Aggregation," *J. Neurosci. Res.* 75(2):162-71, 2004.

Longo and Finch, "Nonfibrillar Aβ 1-42 (ADDL) Causes Aconitase Inactivation and Iron-dependent Neurotoxicity," *Society for Neuroscience* 25: 2129, 1999.

Masters et al., "Amyloid Plaque Core Protein in Alzheimer's Disease and Down Syndrome," *Proc. Natl. Acad. Sci. U.S.A.* 82:4245-4249, 1985.

McKhann et al., "Clinical Diagnosis of Alzheimer's Disease: Report of the NINCHS-ADRDA Work Group Under the Auspices of Department of Health and Human Services Task Force on Alzheimer's Disease," *Neurology* 34:939-944, 1994.

Morgan et al., "Aβ Peptide Vaccination Prevents Memory Loss in an Animal Model of Alzheimer's Disease," *Nature* 408:982-985, 2000.

Moss et al., "The Peptide KLVFF-K$_6$ Promotes β-Amyloid(1-40) Protofibril Growth by Association but Does Not Alter Protofibril Effects on Cellular Reduction of 3-(4,5-Dimethylthiazol-2-yl)-2,5-Diphenyltetrazolium Bromide (MTT)," *Mol. Pharmacol.* 64(5):1160-8, 2003.

Motter et al., "Reduction of β-Amyloid Peptide$_{42}$ in the Cerebrospinal Fluid of Patients with Alzheimer's Disease," *Ann. Neurol.* 38:643-648, 1995.

Nichols et al., "Amyloid-β Aggregates Formed at Polar-Nonpolar Interfaces Differ From Amyloid-β Protofibrils Produced in Aqueous Buffers," *Microsc. Res. Tech.* 67(3-4):164-74, 2005.

Nicoll et al., "Neuropathology of Human Alzheimer Disease After Immunization With Amyloid-β Peptide: A Case Report," *Nature Med.* 9(4):448-452, 2003.

Oda et al., "Clusterin (apoJ) Alters the Aggregation of Amyloid β-Peptide (Aβ 1-42) and Forms Slowly Sedimenting Aβ Complexes that Cause Oxidative Stress," *Exp. Neurol.* 136:22-31, 1995.

Oda et al., "Purification and Characterization of Brain Clusterin," *Biochem. Biophys. Res. Comm.* 204:1131-6, 1994.

O'Nuallain et al., "Conformational Abs Recognizes a Generic Amyloid Fibril Epitope," *Proc. Natl. Acad. Sci. U.S.A.* 99:1485-1490, 2002.

Palmert et al., "The β-Amyloid Protein Precursor of Alzheimer Disease Has Soluble Derivatives Found in Human Brain and Cerebrospinal Fluid," *Proc. Natl. Acad. Sci. U.S.A.* 86:6338-6342, 1989.

Pirttilä et al., "Soluble Amyloid β-Protein in the Cerebrospinal Fluid From Patients with Alzheimer's Disease, Vascular Dementia and Controls," *J. Neurol. Sci.* 127:90-95, 1994.

Ponte et al., "A New A4 Amyloid mRNA Contains a Domain Homologous to Serine Proteinase Inhibitors," *Nature* 331:525-527, 1988.

Qin et al., "Effect of 4-Hydroxy-2-Nonenal Modification on Alpha-Synuclein Aggregation," *J. Biol. Chem.* 282(8):5862-5870, 2007.

Roher et al., "Morphology and Toxicity of Aβ-(1-42) Dimer Derived from Neuritic and Vascular Amyloid Deposits of Alzheimer's Disease," *J. Biol. Chem.* 271:20631-20635, 1996.

Russo et al., "Presenilin-1 Mutations in Alzheimer's Disease," *Nature* 405:531-532, 2000.

Rzepecki et al., "Prevention of Alzheimer's Disease-Associated Aβ Aggregation by Rationally Designed Nonpeptitdic β-Sheet Ligands," *J. Biol. Chem.* 279:47497-47505, 2004.

Selkoe, "Cell Biology of the Amyloid β-Protein Precursor and the Mechanism of Alzheimer's Disease," *Ann. Rev. Cell Biol.* 10:373-403, 1994.

Selkoe, "Normal and Abnormal Biology of the β-Amyloid Precursor Protein," *Ann. Rev. Neurosci.* 17:489-517, 1994.

Serpell, "Alzheimer's Amyloid Fibrils: Structure and Assembly," *Biochim. Biophys. Acta* 1502:16-30, 2000.

Seubert et al., "Isolation and Quantification of Soluble Alzheimer's β-Peptide From Biological Fluids," *Nature* 359:325-327, 1992.

Sherrington et al., "Cloning of a Gene Bearing Missense Mutations in Early-Onset Familial Alzheimer's Disease," *Nature* 375:754-760, 1995.

Shtilerman et al., "Molecular Crowding Accelerates Fibrillization of α-Synuclein: Could an Increase in the Cytoplasmic Protein Concentration Induce Parkinson's Disease?" *Biochemistry* 41:3855-3860, 2002.

Sigurdsson et al., "Immunization With a Nontoxic/Nonfibrillar Amyloid-β Homologous Peptide Reduces Alzheimer's Disease-Associated Pathology in Transgenic Mice," *Am. J. Pathol.* 159(2):439-447, 2001.

Solomon et al., "Disaggregation of Alzheimer β-amyloid by Site-directed mAb," *Proc. Natl. Acad. Sci. U.S.A.* 94:4109-4112, 1997.

Solomon et al., "Monoclonal Antibodies Inhibit In Vitro Fibrillar Aggregation of the Alzheimer Beta-amyloid Peptide," *Proc. Natl. Acad. Sci. U.S.A.* 93:452-455, 1996.

Solomon et al., "Monoclonal Antibodies Restore and Maintain the Soluble Conformation of β-amyloid Peptide," *Neurobiol. Aging*, vol. 17, No. 4, Suppl. 152, 1996.

Soto et al., "The Conformation of Alzheimer's β Peptide Determines the Rate of Amyloid Formation and Its Resistance to Proteolysis," *Biochem. J.* 1:314:701-7, 1996.

Srinivasan et al., "ABri Peptide Associated with Familial British Dementia Forms Annular and Ring-Like Protofibrillar Structures," *Amyloid* 11(1):10-3, 2004.

St. George-Hyslop et al., "The Genetic Defect Causing Familial Alzheimer's Disease Maps on Chromosome 21," *Science* 235:885-890, 1987.

St. George-Hyslop et al., "Genetic Linkage Studies Suggest that Alzheimer's Disease is Not a Single Homogeneous Disorder," *Nature* 347:194-197, 1990.

Stine et al., "The Nanometer-Scale Structure of Amyloid-β Visualized by Atomic Force Microscopy," *J. Prot. Chem.* 15(2):193-203, 1996.

Stine et al., "Supramolecular Structures of Aβ Aggregates and Cellular Responses," Biophysical Journal Program and Abstracts:40th Annual Meeting Feb. 17-21, 1996, *Biophys J.* 70: Abstract 239.

Suzuki et al., "An Increased Percentage of Long Amyloid β Protein Secreted by Familial Amyloid β Protein Precursor ($\beta APP_{717}$) Mutants," *Science* 264:1336-1340, 1994.

Vickers, "A Vaccine Against Alzheimer's Disease: Developments to Date," *Drugs Aging* 19(7):487-494, 2002.

Walsh et al., "Amyloid β-Protein Fibrillogenesis. Detection of a Protofibrillar Intermediate," *J. Biol. Chem.* 272:22364-22372, 1997.

Walsh et al., "Amyloid β-Protein Fibrillogenesis. Structure and Biological Activity of Protofibrillar Intermediates," *J. Biol. Chem.* 274(35):25945-25952, 1999.

Walsh et al., "Naturally Secreted Oligomers of Amyloid β Protein Potently Inhibit Hippocampal Long-Term Potentiation In Vivo," *Nature* 416:535-539, 2002.

Walsh et al., "Amyloid-β Oligomers: Their Production, Toxicity and Therapeutic Inhibition," *Biochem. Soc. Trans.* 30:552-7, 2002.

Walsh et al., "Oligomers on the Brain: The Emerging Role of Soluble Protein Aggregates in Neurodegeneration," *Protein Pept. Lett.*, 11:213-28, 2004.

Ward et al., "Fractionation and Characterization of Oligomeric, Protofibrillar Forms of β-Amyloid Peptide," *Biochem. J.* 348:137-144, 2000.

Weidemann et al., "Identification, Biogenesis, and Localization of Precursors of Alzheimer's Disease A4 Amyloid Protein," *Cell* 57:115-126, 1989.

Weiner et al., "Nasal Administration of Amyloid-β Peptide Decreases Cerebral Amyloid Burden in a Mouse Model of Alzheimer's Disease," *Annals Neurol.* 48(4):567-579, 2000.

Westlind-Danielsson and Arnerup, "Spontaneous In Vitro Formation of Supramolecular β-Amyloid Structures, "βamy Balls", by β-Amyloid 1-40 peptide," *Biochemistry* 40:14736-43, 2001.

Williams et al., "Structural Properties of Aβ Protofibrils Stabilized by a Small Molecule," *Proc. Natl. Acad. Sci. U.S.A.* 102(20):7115-20, 2005.

Wirak et al., "Deposits of Amyloid β Protein in the Central Nervous System of Transgenic Mice," *Science* 253:323-325, 1991.

Ye et al., "Protofibrils of Amyloid β-Protein Inhibit Specific $K^+$ Currents in Neocortical Cultures," *Neurobiol. Dis.* 13:177-190, 2003.

Yoritaka et al., "Immunohistochemical Detection of 4-Hydroxynonenal Protein Adducts in Parkinson Disease," *Proc. Natl. Acad. Sci. U.S.A.* 93:2696-2701, 1996.

Yoshikai et al., "Genomic Organization of the Human Amyloid Beta-protein Precursor Gene," *Gene* 87:257-263, 1990.

* cited by examiner

▼▼▼  Protofibrillar Aβ40Arc
─○─○─○─  Protofibrillar Aβ40wt+Arc (1:1)
●●●  Protofibrillar Aβwt

ANTIBODIES SPECIFIC FOR AMYLOID BETA PROTOFIBRIL

CROSS-REFERENCE TO RELATED APPLICATIONS

This application is a divisional of U.S. Ser. No. 12/051,785, filed Mar. 19, 2008, which is a divisional of U.S. Ser. No. 11/654,508, filed Jan. 18, 2007, now U.S. Pat. No. 7,700,719, which, in turn, is a divisional of U.S. Ser. No. 09/899,815 filed Jul. 9, 2001, now U.S. Pat. No. 7,179,463, which, in turn, claims priority to European Application No. 00202387.7, filed Jul. 7, 2000 and benefit of U.S. Ser. No. 60/217,098 filed Jul. 10, 2000, the contents of which are incorporated by reference in the entirety.

FIELD OF THE INVENTION

The present invention relates to prevention and treatment of Alzheimer's disease (AD). More specifically, the invention relates to use of a non-wild type protofibril or compound(s) with protofibril forming ability for active immunisation in the purpose of treating or preventing AD. The invention further relates to a peptide, Aβ-Arc, with high protofibril forming activity as well as several applications thereof, such as antibodies against said peptide for passive immunisation against AD.

BACKGROUND OF THE INVENTION

Alzheimer's disease (AD) is a progressive disease known generally as senile dementia. The disease falls into two categories, namely late onset and early onset. One form of this latter AD type runs in families and it is known as familial AD.

Both types of AD are characterized by two types of lesions in the brain: senile plaques and neurofibrillary tangles. Senile plaques are areas of disorganized neuropil up to 150 mm across with extracellular amyloid deposits at the center. Neurofibrillary tangles are intracellular deposits consisting of two filaments twisted about each other in pairs.

Aβ also referred to as amyloid β peptide (AβP) is a highly aggregating small polypeptide having a molecular weight of approximately 4,500. This protein is a cleavage product of a much larger precursor protein referred to as amyloid precursor protein (APP). The Aβ protein comprises 39-42 amino acids. There are at least five distinct isoforms of APP: 563, 695, 714, 751, and 770 amino acids, respectively (Wirak et al. (1991)). The Aβ protein segment comprises approximately half of the transmembrane domain and approximately the first 28 amino acids of the extracellular domain of an APP isoform.

APP is a transmembrane protein which is highly expressed in all parts of the body, and which has several important biological functions. Proteolytic processing of APP in vivo is a normal physiological process. Carboxy-terminal truncated forms of APP695, APP751, and APP770 are present in brain and cerebrospinal fluid (Palmert et al. (1989)) (Weidemann et al (1989)). There are probably two main metabolic pathways: one non-amyloid-forming and one amyloid-forming pathway. The amyloid forming non-normal pathway produces the Aβ protein polypeptide which is prone to form dense amyloidogenic aggregates that are resistant to proteolytic degradation and removal. The resultant Aβ protein aggregates presumably are involved in the formation of the abundant amyloid plaques and cerebrovascular amyloid that are the neuropathological hallmarks of AD.

In AD brains, the Aβ peptide forms virtually insoluble amyloid fibrils that accumulate into senile plaques. The Aβ fibrillization process is a complex multistep reaction. A group of distinct intermediary Aβ species of the fibrillization reaction, the protofibrils, were recently identified (Walsh et al. (1997)), (Walsh et al. (1999), (Harper et al. (1999)).

The most common Aβ form in cerebrospinal fluid (CSF) and plasma comprises 40 amino acids (Aβ40), but an Aβ comprising 42 amino acids (Aβ42) is the most common form in plaques (Scheuner et al. (1996)). This longer form tends to aggregate more rapidly and it is believed that it is more pathogenic than Aβ40.

Many patients get Alzheimer's disease spontaneously with unknown ethiology, but there are also several hereditary components involved. Disease-causing mutations in genes on chromosomes 1, 14, and 21, respectively, have been discovered, and these mutations might explain as much as 50% of disease forms starting very early (<50 years)(St. George-Hyslop et al. (1987), (Sherrington et al. (1995)).

The first gene associated with Alzheimer's disease was the gene encoding the amyloid precursor protein APP on chromosome 21. Different mutations of this gene result in unusual hereditary forms of the disease. Several pathogenic mutations have been identified in the (APP) gene, all located close to the major APP processing sites. These processing sites are either located adjacent to the boundaries of the Aβ domain in APP (the β- and γ-secretase sites) or within the Aβ sequence itself (α-secretase site).

The only known AD mutation close to the β-secretase site, the Swedish mutation (Mullan, et al., (1992)), discloses a double mutation (Lys670Asn/Met671Leu) of the APP gene in a large Swedish family, in which family the disease starts early and has a high penetrating power. The mutation produces a large increase of Aβ production, an elevation of both Aβ42 and Aβ40 in plasma from mutation carriers and in conditioned cell media.

Other APP mutations have been described. All result in Alzheimer's disease with an early age of onset having an autosomal dominant heredity pattern. Pathogenic mutations within the Aβ sequence, located close to the α-secretase site, result in a phenotype different from AD, with massive amyloid accumulation in cerebral blood vessel walls. Two mutations at codons 692 and 693, namely the Dutch (Glu693Gln) and the Flemish (Ala692Gly) mutations, have been reported (Levy et al. (1990)), (van Broeckhoven et al. (1990)), (Hendriks et al. (1992)). Patients having these mutations suffer from cerebral haemorrhage and vascular symptoms. The vascular symptoms are caused by aggregation of Aβ in blood vessel walls (amyloid angiopathy). A third pathogenic intra-Aβ mutation was recently discovered in an Italian family (E693K), with clinical findings similar to the Dutch patients (Tagliavini, et al. (1999)).

Different pathogenic mechanisms have been proposed for the Dutch and Flemish mutations. It has been observed that the Flemish mutation leads to increased Aβ levels while a reduced ratio of Aβ42/40 was seen in media from cells transfected with the Dutch mutation (De Jonghe, et al. (1998)). Investigations of synthetic Aβ peptides have indicated that the Dutch mutation, but not the Flemish, accelerates the fibril formation compared to wild-type (wt) peptide (Walsh et al. (1997)).

As reported by Kamino et al. 1992, another APP E693 variant wherein Glu is substituted for Gly at APP E693, has previously been seen in one individual. It could not be unambiguously determined to be responsible for AD, though. This case originated from a family with similar clinical characteristics for AD and definitive AD was confirmed at autopsy.

However, in this family the mutation could only be detected in one of two demented siblings.

Mice transgenic for APP mutations show many of the pathological features of Alzheimer disease, including deposition of extracellular amyloid plaques, astrocytosis and neuritic dystrophy. In recent studies by (Schenk et al (1999)) it was reported that immunization with Aβ42 wild-type peptide is both preventive in transgenic mice, but also that Aβ containing plaques can be greatly reduced in the brain of transgenic mice immunized with the peptide.

However, due to the large costs and suffering that are associated with Alzheimer's disease, there is still a need for improved methods for treatment and prevention thereof.

Likewise, there is a need for a method for screening compounds that could constitute a part of future pharmaceutical preparations for treating and perhaps curing Alzheimer's disease.

SUMMARY OF THE INVENTION

The present invention relates to an active immunisation against AD which will have a much more profound effect in the treatment of Alzheimer's disease, than using the wild-type peptide. Immunization according to the invention will yield antibodies directed to protofibrils, as the immunogen is a protofibril or compound(s) with greatly increased protofibril formation properties. These antibodies, generated in the periphery, will cross the blood brain barrier and mediate clearance of AD in the brain in a protofibril state.

In present invention use is made of a pathogenic AD mutation at codon 693 (Glu693Gly), named the 'Arctic mutation', located within the Aβ peptide domain of the APP gene, more closely position 22 of the AD-Arc peptide. Carriers of this mutation develop progressive dementia with clinical features typical of AD without symptoms of cerebrovascular disease. Said AD is distinctly characterised by accelerated formation of protofibrils comprising mutated Aβ peptides (40Arc and/or 42Arc) compared to protofibril formation of wild type Aβ peptides.

Thus, in a first aspect the invention relates to use of a non-wild type protofibril or compound(s) with protofibril forming ability for immunisation for prevention or treatment of Alzheimer's disease (AD). Preferably, these protofibril or compounds) have enhanced protofibril forming ability and/or enhanced immunogenicity compared to the wild-type counterparts. Protofibril chemistry has been described by, inter alia, Serpell (2000).

Preferably, the protofibril or compound(s) with protofibril forming ability comprises the following amino acid sequence KLVFFAEDV (SEO ID NO:2). The Aβ-42 fibrillisation process involves transitional conformation changes from α-helix via random coil to β-sheet. The stable α-helix sequence of residues 16-24 (KLVFFAEDV (SEO ID NO:2)) apparently plays an important role in this process.

The protofibril or compound(s) with protofibril forming ability may be mutated or modified in relation to corresponding wild-type counterparts. Changes in the KLVETAEDV (SEO ID NO:2) sequence will affect the fibrillisation process. For example, changes of the charged amino acids Glu22 and Asp23 into neutral amino acids will induce a random coil structure in the Aβ peptide. Furthermore, deprotonation of other amino acids such as Asp7, Glu11 and His 6, 13 and 14 in the N-terminal end, has been suggested to destabilize the α-helix, leading to initiation of the fibrillation process. Another example is mutations leading to increased irninunogenicity in man by using amino acids from mouse Aβ at specific positions, e.g. Gly 5, Phe10 Arg13. Furthermore, amino acid 13 in Aβ is known to be part of a heparan sulphate binding motif (13-16; His, His, Gln, Lys (SEO ID NO:5)) in human, which has been speculated to be involved in AD disease mechanism (inflammation) (Giulian et al. (1998)). In mouse, His 16 is exchanged for Arg 13 destroying the heparan sulphate binding site. Interestingly, mice have never been observed to develop AD. Hence, the use of Aβ-Arc/Arg13 as an immunogen would be a way to lower possible inflammatory side effects, elicited with Aβ peptides with intact heparan sulphate binding motif.

Preferably, the protofibril or compound(s) with protofibril forming ability comprises an Aβ peptide (β-amyloid protein) and repeats thereof, such as dimeric, oligomeric or multimeric forms). In a preferred embodiment the protofibril or compound(s) with protofibril forming ability comprises a Aβ peptide related to AD, In another embodiment the protofibril or compound(s) with protofibril forming ability comprises α-synuclein (SEO ID NO:11).

There exists a form of dementia characterised by patients having clusters in the brain of a structure called Lewy bodies. This form of dementia comprises about 20% of all dementia, Patients with Lewy bodies show, inter alia, Parkinson symptoms with progressive cognitive dysfunction. However, some patients also exhibit Alzheimer symptoms and this is called "Lewy variant of Alzheimer". The main component of the Lewy bodies is the protein α-synuclein (SEO ID NO:11). Two mutations in α-synuclein have been identified Ala53Thr (SEO ID NO:12) and Ala30Pro (SEO ID NO:13). These mutations lead to dominant heritage of Parkinson's disease. These mutations affect the structure/solubility of α-synuclein and leads to formation of protofibrils. (Conway et al. (2000)).

The Aβ peptide is preferably Aβ-Arc as disclosed in SEQ ID NO 1. Aβ-Arc comprises 39, 40 or 42 amino acids but may also be shorter as long as the protofibril forming ability is maintained.

The protofibril or compound(s) with protofibril forming ability may be used in combination with Aβ peptides having known mutations, such as the Dutch (SEO ID NO:6), Flemish (SEO ID NO:7), Italian (SEO ID NO:8) mutation described above as well as the Iowa (SEO ID NO:9) mutation (D694N) (Grabowski et al., 2001). The Aβ peptide may comprise one or more of these and/or other mutations. Alternatively, a cocktail of different Aβ peptides with different mutations is used.

In a second aspect, the invention relates to a peptide, Aβ-Arc, having the amino acid sequence disclosed in SEQ ID NO 1 comprising a glycine at position 22 instead of glutamic acid compared to wild type Aβ peptide. The peptide may be natural, synthetic or recombinantly produced. For the purposes of the invention the peptide may be used in monomeric, dimeric, oligomeric, protofibril or multimeric form.

The invention also relates to nucleic acid encoding the above peptide as well as a vector comprising the nucleic acid. The vectors for expressing the polypeptides of the invention require that the nucleic acid be "operatively linked." A nucleic acid is operatively linked when it is placed into a functional relationship with another nucleic acid sequence.

This vector may be inserted in a host cell. Such a host cell can be used to recombinantly produce the peptide of the invention for pharmaceutical or diagnostic use as well for research purposes. The peptide may also be produced synthetically and be purified by HPLC, RP-HPLC, SEC-HPLC.

In a further aspect, the invention relates to a transgenic non-human animal comprising the above vector. Furthermore, the invention relates to a transgenic non-human animal comprising a vector comprising the entire APP gene corresponding to NCBI database, accession no XM_009710, *Homo sapiens* amyoid β(A4) precursor protein (protease nexin-II, Alzheimer's disease)(APP), mRNA. However, the APP gene for use in the invention comprises the Arctic mutation, i.e. nucleotide number 2225 is mutated from A to G leading to an amino acid substitution from Glutamic acid to Glycine. The transgenic animal may be used for modelling Alzheimer's disease and testing for therapeutic treatment efficacy. This transgenic animal will bear the entire APP gene comprising the Arctic mutation. This gene is preferably under control of a strong promoter, such as the prion-promoter. The APP gene may contain further mutations, besides the Arctic mutation.

The transgenic animal expresses a human APP or a fragment thereof which encodes glycine instead of glutamic acid at codon 693. Preferably, the animal expresses neuropathological characteristics of AD. Preferably, the mutated APP is expressed in cells which normally expresses the naturally-occurring endogenous APP gene (if present). Typically, the non-human animal is a mouse. Such transgenes typically comprises an Arctic mutation APP expression cassette, wherein a linked promoter and, preferably, an enhancer drive expression of structural sequences encoding a heterologous APP polypeptide comprising the Arctic mutation.

Such transgenic animals are usually produced by introducing the transgene or targeting construct into a fertilized egg or embryonic stem (ES) cell, typically by microinjection, electroporation, lipofection, or biolistics. The transgenic animals express the Arctic mutation APP gene of the transgene. (or homologously recombined targeting construct), typically in brain tissue. Alzheimer phenotype and neuropathology is caused by protofibril formation. Such animals are suitable for use in a variety of disease models and drug screening uses, as well as other applications.

In yet a further aspect, the invention relates to antibodies against the Aβ peptide of SEQ ID NO 1. The antibodies may be monoclonal or polyclonal or antibody fragments. Preferably the antibodies are humanized for use in passive immunisation for prevention or therapy against AD. Thus, antibodies which react with the unique epitope created by glycine at codon 693 are provided.

Another aspect of the invention relates to a pharmaceutical composition, comprising the above peptide and physiologically acceptable excipients for human and veterinary use. The preparation may comprise adjuvants for vaccination purposes. The administration route may be s.c., i.m., oral or nasal.

In a further aspect, the invention relates to use of the above Aβ peptide for high throughput screening to find substances with anti-protofibrillar activity.

In a further aspect, the invention relates to a method for prevention or treatment of AD, comprising the step:

decreasing the formation of Aβ protofibrils and/or lower merit forms thereof in a subject having, or suspected of having, AD.

The decreasing step above may be by active immunisation with a profibril or compound(s) with protofibril forming ability for prevention or treatment of Alzheimer's disease (AD), wherein said protofibril or compound(s) have enhanced protofibril forming ability and/or enhanced immunogenicity compared to the wild-type counterparts.

Alternatively, the decreasing step above is by passive immunisation with antibodies against protofibrils or compound(s) with protofibril forming ability, such as Aβ-Arc. The passive immunisation may be in combination with antibodies against other Aβ peptides with mutations/modifications leading to increased protofibril formation and/or immunogenicity, preferably AD related mutations.

Antibodies generated against the human Aβ sequence containing the Arctic mutation are directed towards Aβ protofibrils and therefore are of therapeutic value in the treatment of Alzheimer's disease. Because the Aβ peptide is in a protofibril conformation when used as an immunogen, antibodies against Aβprotofibrils are generated. Availability of such antibodies opens up possibilities for the development of an efficient and lasting vaccination for the prevention and treatment of Alzheimer's disease.

In another alternative the decreasing step of the method according to the invention is by administration of agents with anti-protofibrillar activity.

In yet a further aspect of the invention, a combination of the vaccine or passive immunization with monoclonal antibodies or compounds with anti-fibrillar activity with one or several other AD treatments such as, acetylcholinesterase inhibitors, nootropics, anti-inflammatory drugs, estrogen, neurotrophic factor agonists, β-secretase inhibitors, γ-secretase inhibitors and α-secretase agonists, can improve AD treatment efficacy. The rational is that these substances/treatments work with completely different mechanisms of action and hence can be combined to the benefit for the AD patient.

DETAILED DESCRIPTION OF THE INVENTION

The basis of the present invention is a pathogenic amyloid precursor protein (APP) mutation located within the Aβ sequence at codon 693 (E693G), causing AD in a family from northern Sweden. Surprisingly, carriers of this "Arctic" mutation show decreased Aβ42 and Aβ40 levels in plasma. This finding is corroborated in vitro, where the Aβ42 concentration was low in conditioned media from cells transfected with $APP_{E693G}$. Fibrillization studies demonstrate that Aβ peptides with the Arctic mutation (Aβ40Arc) form protofibrils at a much higher rate and in larger quantities than wild-type (wt) Aβ (Aβ40 wt). The unique finding of decreased Aβ plasma levels in the Arctic AD family highlights the complexity of the disease and is likely to reflect a novel pathogenic mechanism. The mechanism disclosed in the present invention involves a rapid Aβ protofibril formation leading to accelerated build-up of insoluble Aβ intra- and/or extracellularly.

In the present invention, the single amino acid substitution Glu to Gly at position 22 in the Aβ4040Arc molecule was found to cause a dramatic increase in rate and capacity to form protofibrils compared to the Aβ40wt peptide. Thus, when Aβ42Arc and Aβ40Arc are formed in the brain it is likely that they are more prone to be retained by cellular systems since the accelerated drive to form protofibrils enhances both Aβ bulk and insolubility. Thus, factors promoting protofibril formation should be considered in the pathogenesis of sporadic AD. Increased protofibril formation is probably also operating in these more common forms of the disease. Indeed, the findings of the present invention open new avenues for possible therapeutic intervention using drugs targeted at preventing protofibril formation.

Studies on the Arctic mutation of the present invention have demonstrated a previously not described pathogenic mechanism for Alzheimer's disease through increased formation of Aβ protofibrils. Aβ with the Arctic mutation formed more stable protofibrils and at a much higher rate and in larger quantities than wild-type Aβ, even in the presence of equimolar amounts of wild-type Aβ. The formation is accelerated at least 2-10 times compared to protofibrill formation of wild type Aβ peptides. The implication of this finding is that the dangerous species in the amyloid forming pathway that eventually leads to Alzheimer's disease is not the Aβ fibrils, but a form of the peptide that appears earlier in the fibril maturation process, the protofibrils. One implication of the findings related to the present invention is that it is important to prevent the formation of protofibrils in order to be able to prevent and treat Alzheimer's disease.

Non-human animals comprising transgenes which encode. Arctic mutation APP can be used commercially to screen for agents having the effect of lowering the formation of Aβ protofibrils. Such agents can be developed as pharmaceuticals for treating abnormal APP processing and/or Alzheimer's disease, amongst other neurodegenerative conditions in humans and animals, such as dogs. The transgenic animals of the present invention exhibit abnormal APP processing and expression, and can be used for pharmaceutical screening and as disease models for neurodegenerative diseases and APP biochemistry.

FIGURE LEGENDS

The present invention will now be further described with reference to the enclosed figures, in which:

FIG. 1 shows kinetics of soluble forms of Aβ1-40wt (a), Aβ1-40Arc (b) and protofibril formation of Aβ1-40wt, Aβ1-40Arc vs a mixture of Aβ1-40wt+Arc (1:1) (c). The Aβ1-40Arc peptide (92 µM) rapidly forms protofibrils (black dots) in comparison to the Aβ1-40wt peptide (88 µM), which mainly is in monomeric (dimeric (grey dots) form, data is taken from one experiment, representative of three (a and b). The protofibril formation rate was monitored during the first seven hours and the kinetics for the pure peptides (Aβ1-40wt and Aβ1-40Arc at 50 µM) was compared to the protofibril formation rate of a 1:1 mixture (50 µM) of Aβ1-40wt+Arc (c).

Figure 2:
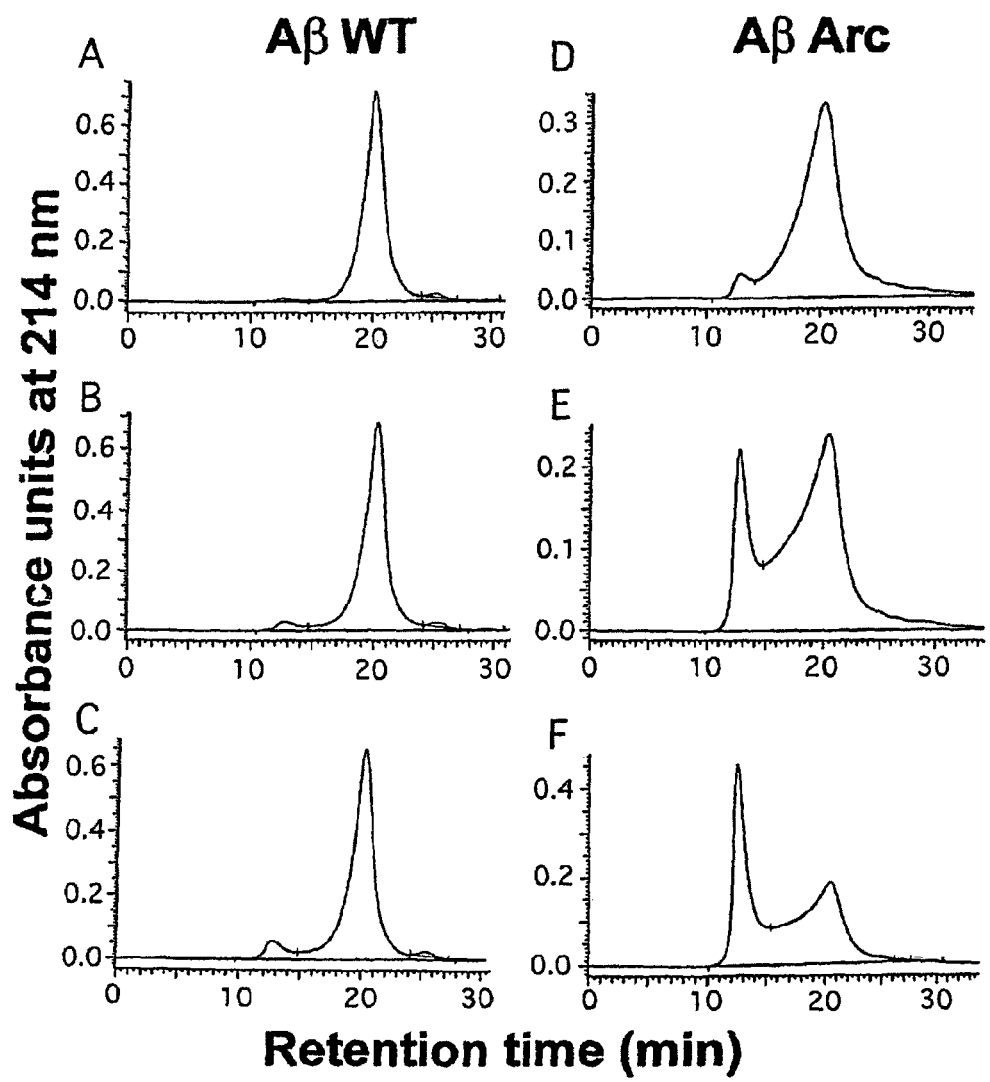

FIG. 2 depicts elution profiles showing Aβ40 wt (a-c) versus Aβ40Arc (d-f) at 5 (a,d), 45 (b,e) and 125 (c,f) min of incubation. Accelerated protofibril (p) formation along with a parallel decline in the monomeric/dimeric (m/d) Aβ levels could be observed for Aβ40Arc (d-f) as compared to Aβ40wt (a-c). Data is from one experiment, representative of four. Initial peptide concentrations were 143 µM and 138 µM for Aβ40wt and Aβ40Arc, respectively.

EXAMPLES

The following examples are provided for illustration and are not intended to limit the invention to the specific example provided.

Example 1

Identification of the Arctic Mutation

An APP mutation (E693G) in a family from northern Sweden, named the "Arctic" family, is identified, which spans over four generations. The family was screened for mutations in exons 16 and 17 of the APP gene by single strand conformation polymorphism analysis (SSCP) (L. Forsell, L. Lannfelt, (1995)). An abnormal mobility pattern was observed in exon 17. Sequencing revealed an A->G nucleotide substitution, representing a glutamic acid to a glycine substitution at APP codon 693 (E693G), corresponding to position 22 in the Aβ sequence. Venous blood was drawn into tubes containing EDTA and DNA was prepared according to standard procedures. SSCP was performed. To sequence exon 17 of the APP gene a 319 bp fragment was amplified with the following primers 5'-CCT CAT CCA AAT GTC CCC GTC ATT-3' (SEQ ID NO:3) and 5'-GCC TAA TTC TCT CAT AGT CTT AAT TCC CAC-3' (SEQ ID NO:4). The PCR products were purified with QIAquick PCR purification kit (Qiagen) prior to sequencing. Direct sequencing was performed in both 3' and 5' direction using the same primers and the BIG Dye cycle sequencing protocol (PE Biosystems) and were then analyzed on an ABI377 automated sequencer (PE Biosystems). The Arctic mutation was seen in one family and not in 56 controls or 254 cases with dementia. Carriers of the arctic mutation showed no vascular symptoms. The mutation was further verified by restriction analysis, since it destroyed a MboII restriction site. The mutation was fully penetrant as no escapees were found. Two-point linkage analysis was performed between the mutation and affection status in the family with an age-dependent penetrance, giving a lod score of 3.66 at recombination fraction 0.00. Two-point lod score was calculated using Mlink from the linkage package (version 5.1) at each of the following recombination fractions 0.00, 0.10, 0.20, 0.30 and 0.40 (q males=q females). A single-locus model with an autosomal dominant inheritance was assumed, which was compatible with the inheritance as it appeared in the pedigree. A cumulative age dependent penetrance was assigned from the known ages of onset in the family. Individuals were put into different liability classes depending on the age at onset (affected) or age at last examination (unaffected). The disease gene frequency and the marker allele frequency were estimated to be 0.001 and the phenocopy rate was set to 0.0001.

Example 2

Clinical Symptoms in Carriers of the Arctic Mutation

The family with the "Arctic" mutation was clinically and genealogically investigated. In this family, the mean age of onset was 56.6 years and the mean duration of the disease was 7 years (n=5).

The first symptom in most cases in this family was an insidious loss of memory for recently acquired information. Symptoms before clinical manifestation of Alzheimer's disease were decreased power of concentration and difficulties in handling stress situations. All affected individuals in generation IV had an early retirement pension because of the disease. The patients in generation IV were investigated by magnetic resonance imaging (MRI), computed tomography (CT) and electroencephalography (EEG) which confirmed the diagnosis of Alzheimer's disease. In four individuals CT and MRI did not demonstrate signs of stroke or cerebral haemorrhage.

Example 3

Decreased Aβ Plasma Levels in Carriers of the Arctic Mutation

Pathogenic APP mutations have been shown to affect APP processing, as reflected in an increase of either total Aβ or Aβ42 in the plasma of affected family members. The Arctic mutation is located in a region different from other AD-causing mutations. It was investigated as to whether the mutation manifested itself by affecting Aβ plasma levels. Plasma from nine mutation carriers, of which four were symptomatic, and eleven non-carriers in the family, were analysed by well-characterized sandwich ELISA systems, specifically detecting Aβ42 (BAN50/BC05) and A1340 (BAN50/BA27) (Suzuki et al. 1994)). To reassure that the Arctic mutation did not change any of the antibody recognition sites Aβ40wt and Aβ40Arc peptides were tested and found to be recognized equally well. Furthermore, plasma was spiked with synthetic peptides, revealing that both AβArc and Aβ wt peptides were recovered by ELISA to the same extent. The data obtained was analyzed by non-parametric Mann-Whitney analysis. The Aβ42 plasma concentration was 11.7±3.9 fmol/ml and 16.0±5.6 fmol/ml in mutation carriers and non-carriers, respectively, representing a 27% reduction of Aβ42 in the mutation carriers (p=0.04). The Aβ40 plasma concentration was 105±22 fmol/ml and 141±34 fmol/ml in mutation carriers and non-carriers, respectively, representing a 26% reduction of Aβ40 in the mutation carriers (p=0.01). The Aβ42/40 ratio was calculated for each individual, but no significant difference was found (p=0.13). In conclusion, concentrations of both Aβ42 and Aβ40 were unexpectedly and significantly reduced in individuals carrying the Arctic mutation.

Example 4

Aβ Levels in Cell Culture

The effect of the Arctic mutation on Aβ formation was further investigated in vitro in transiently transfected HEK293 cells. APPwt was compared to the following mutations:

Arctic ($APP_{E693G}$), Dutch ($APP_{E693Q}$), Italian ($APP_{E693K}$) and Flemish ($APP_{A692G}$). Constructs containing the Swedish double mutation ($APP_{Swe}$) and one APP mutation at codon 717 ($APP_{V717F}$), both with well-studied APP processing characteristics (Hardy (1997)), were used as positive controls. The mutations were introduced to APP695 cDNA in pcDNA3 using QuikChange™ Site-Directed Mutagenesis Kit according to the manufacturers instructions (Stratagene). The mutated constructs were verified by sequencing. For the ELISA measurements, HEK293 cells were seeded in six-well dishes and transfected with the different constructs using FuGENE™ 6 Transfection Reagent (Roche Diagnostics) according to the manufacturers instructions. 24 h after transfection, the cells were conditioned 48 h in OptiMEM containing 5% newborn calf serum. After withdrawal of the media for ELISA measurements, the APP expression in the cells were investigated by western blot using monoclonal antibody 22C11 (Roche Diagnostics). Media was conditioned and analyzed for Aβ levels by the same Aβ42- and Aβ40-specific sandwich ELISA systems as used for human plasma (Citron, et al. (1997)). The Aβ42 and Aβ40 concentrations and Aβ42/40 ratios are shown in Table 1.

TABLE 1

Aβ42/40 ratio and Aβ42 and Aβ40 levels in conditioned media from transiently transfected HEK293 cells

| APP constructs | Aβ42/40 ratio (%) ± SD | Aβ42 ± SD (fmol/ml) | Aβ40 ± SD (fmol/ml) |
|---|---|---|---|
| APPwt | 9.6 ± 0.7 | 13.8 ± 1.0 | 144 ± 6 |
| Arctic (E693G) | 7.5 ± 0.5* | 11.2 ± 0.6 | 149 ± 3 |
| Dutch (E693Q) | 6.6 ± 0.6* | 9.6 ± 0.7 | 147 ± 12 |
| Italian (E693K) | 6.4 ± 0.6* | 8.0 ± 0.7 | 126 ± 17 |
| Flemish (A692G) | 11.7 ± 1.6* | 27.0 ± 2.0 | 232 ± 25 |
| Mock (vector only) | 7.2 ± 2.4 | 2.1 ± 1.0 | 28 ± 5 |

*P = 0.004 in comparision to APPwt

Decreasing Aβ42/Aβ40 ratios could be seen with all mutations at APP 693 (Arctic, Dutch, Italian). This may be due to increased rate of intracellular protofibril formation.

Example 5

Effect of Arctic Mutation on Protofibril Formation

The effect of the single amino acid substitution (Glu22Gly) on amyloid fibrillization kinetics was investigated. Synthetic Aβ1-40 was dissolved in physiological buffer and incubated for different periods of time. After centrifugation, the soluble Aβ in the supernatant, both low molecular weight (monomeric/dimeric) Aβ and protofibrils, were separated and analyzed using size exclusion chromatography (SEC) with UV detection at 214 nm. The morphology of the sedimented insoluble Aβ was visualized using negative stain and transmission electron microscopy (TEM).

Aβ1-40wt was purchased from Bachem, Bübendorf, Switzerland or Biosource International/QCB (Camarillo, Calif., USA) and Aβ1-40Arc from Biosource International/QCB. The peptides were trifluoroacetic salts. They were stored at −20° C. All other chemicals were of highest purity available. Samples of each peptide were incubated, without agitation, at 30° C. in 50 mM $Na_2HPO_4$ $NaH_2PO_4$ (pH 7.4) containing 0.1 M NaCl, for various time-points. Initial peptide concentrations were within the range of 88-143 μM, and were similar for both peptides in each experiment. After centrifugation (17 900×g for 5 min at 16° C.) monomeric/dimeric and protofibrillar Aβ1-40, sampled from the supernatant, were separated using SEC. A Merck Hitachi D-7000 LaChrom HPLC system, having a diode array detector model L-7455, a L-7200 model autosampler and a model L-7100 pump, coupled to a Superdex 75 PC3.2/30 column (Amersham Pharmacia Biotech, Uppsala, Sweden), was used for the chromatographic separation and analysis. Samples were eluted at a flow rate of 0.08 ml/min (ambient temperature) using 50 mM $Na_2HPO_4$ $NaH_2PO_4$(pH 7.4), 0.15 M NaCl. Chromatograms were obtained by measuring UV absorbance at 214 nm. Peak areas for monomeric/dimeric and protofibrillar Aβ were integrated using Merck-Hitachi Model D-7000 Chromatography Data Station Software. The mean of triplicate integrated peak values from the SEC measurements were used to generate each data point shown in FIGS. 1 and 2. In addition, a standard curve was produced by correlating integrated peak areas with peptide concentrations as determined by quantitative amino acid analysis. The concentrations of total (at t=0 h) and soluble peptides remaining in solution after centrifugation were calculated from the standard curve.

SEC analysis of freshly dissolved Aβ1-40wt generated a single elution peak at a retention time of about 20 min (FIG. 2a). This peak represented the monomeric/dimeric forms of Aβ1-40wt (Walsh et al. (1997)). With increasing incubation time a second distinct peak appeared in the gel-excluded fraction with a retention time of about 12 min. This earlier peak contained protofibrils (FIG. 2b, c), as verified by ultracentrifugation, negative stain and TEM of Aβ1-40wt (data not shown), in line with previous findings (Walsh et al. (1997)). Similar retention times were obtained for the Aβ1-40Arc peptide (FIG. 2d-f). However, Aβ40Arc generated protofibrils much faster and in larger quantities than Aβ40wt. Chromatograms from three early time-points of incubation illustrate this difference (FIG. 1). The monomeric/dimeric Aβ40Arc peak declined in parallel with the growth of the protofibrillar peak (FIG. 2d-f). The maximum concentration (111 μM) of Aβ40Arc protofibrils was observed at 6.5 h.

Kinetic studies up to 48 h showed that Aβ 1-40wt generated a small quantity of protofibrils with a maximum concentration at 25 h (FIG. 1a). In contrast, a rapid and significant formation of protofibrils was seen within the first 5 h of incubation with a simultaneous rapid decline in the concentration of the monomeric/dimeric Aβ 1-40Arc peptide (FIG. 1b). Since carriers of the Arctic mutation are heterozygotes they generate both Aβ wt and Aβ Arc, Assuming equimolar in vivo production, the kinetics of protofibril formation was studied in a 1:1 mixture of Aβ 1-40wt (SEQ ID NO:10) and Aβ 1-40Arc. This mixture of peptides showed kinetics that were intermediate to the single peptide curves (FIG. 1c).

Example 6

Morphology of Aβ-Arc

A typical fibrillar morphology of Aβ1-40Arc in sedimented samples from kinetic studies was confirmed by negative stain and TEM. Aβ peptide samples were prepared and incubated as indicated for the kinetic studies, using higher peptide concentrations (617 μM). After 8 days, aggregated Aβ species were sedimented using the same centrifugation parameters as described above. Buffer was removed and pelleted material was suspended in 50 μl water using gentle sonication (2×6s). Eight μl samples were applied to carbon stabilized Formvar film grids (Ted Pella, Inc., Redding, Calif., USA). Samples were negatively stained with 8 μl uranyl acetate (1%) (E. Merck, Darmstadt, Germany). Four grids were prepared for each sample and examined using a Philips CM10 TEM. Samples from pellets sedimented during the kinetic experiments were also examined. Similar to the sedimented Aβ40wt, large mesh-works of AD could be seen in these preparations. Protofibrils could also be discerned in the sedimented samples. The Aβ1-40Arc protofibrils were longer and less curved compared to the Aβ1-40wt protofibrils. Inter-twining of several fibrils was more common in the Aβ40Arc preparations, resulting in larger fibril diameters.

Example 7

Kinetic Studies

Kinetic studies comparing the formation of Aβ40gly22 protofibrils in the presence of a high and a low concentration of NaCl: The experiments examining Aβ40gly22 protofibril and fibril formation, have been performed in 50 mM phosphate buffer supplemented with 100 mM NaCl. They present data that show that the rate and magnitude of Aβ40gly22 protofibril formation is significantly enhanced in the presence of a high NaCl concentration.

Since intra- and extraneuronal NaCl concentrations differ significantly (ca 117 mM vs 30 mM), this finding supports an increased ability of Aβ40gly22 to form protofibrils in the extra-neuronal space where β-amyloid plaques are found.

REFERENCES

Citron, et al. *Nature Med* 3, 67-72 (1997).
Conway, et al., *Proc Nad Aced Sci USA* 97, 571-576 (2000).
De Jonghe, et al., *Neurobiol Disease* 5, 281-286 (1998).
Forsell, Lannfelt, Neurosci Lett 184, 90-93 (1995).
Giulian et al., *J Biol Chem,* 273, 29719-19726, (1998).
Grabowski et al., *Ann Neurol* 49, 697-705 (2001)
Hardy, *Trends Neurosci.* 20, 154-159 (1997).
Harper et al., *Biochemistry* 38, 972-8980 (1999).
Hendriks, et al., *Nature Genet.* 1, 218-221 (1992).
Kamino, et al., *Am J Hum Genet.* 51, 998-1014 (1992).
Levy, et al., *Science* 248, 1124-1126 (1990).
Mullen, et al., *Nature Genet.* 1, 345-347 (1992).
Palmert et al. *PNAS* 86:6338 (1989)
Schenk et al., *Nature,* 400, 173-177 (1999)
Scheuner, et al., *Nature Med* 2, 864-869 (1996).
Serpell L. C. *Biochim. Biophys. Acta,* 1502, 16-30 (2000).
Sherrington et al. *Nature* 375:754 (1995)
St. George-Hyslop et al. *Science* 235:885 (1987)
Suzuki, et al., *Science* 264, 1336-1340 (1994).
Tagliavini, et al., *Alz Report* 2, S28 (1999).
Walsh et al, *J Biol Chem* 272, 22364-22372 (1997).
Walsh et al., *J Biol Chem* 36, 25945-25952 (1999).
Weidemann et al. *Cell* 57:115 (1989)
Wirak et al. *Science* 253:323 (1991)

---

The invention claimed is:

1. A purified antibody or fragment thereof that binds a soluble Aβ protofibril comprising an Aβ40Arc peptide (SEQ ID NO:1).

2. The antibody according to claim 1, wherein said antibody is monoclonal.

3. The antibody according to claim 1, wherein said antibody is humanized.

4. A composition comprising the antibody as in claim 1.

5. A method for treating Alzheimer's disease, said method comprising the step of administering, to a patient having or suspected of having Alzheimer's disease, the antibody according to claim 1.

6. A method for treating Alzheimer's disease, said method comprising the step of administering, to a patient having or suspected of having Alzheimer's disease, the composition of claim 4.

7. The composition of claim 4, said composition comprising a purified monoclonal antibody or fragment thereof that binds a soluble Aβ protofibril comprising an Aβ40Arc peptide (SEQ ID NO:1).

8. The composition of claim 4, said composition comprising a purified humanized antibody or fragment thereof that binds a soluble Aβ protofibril comprising an Aβ40Arc peptide (SEQ ID NO:1).

9. The method of claim 5, said method comprising administering a purified monoclonal antibody or fragment thereof that binds a soluble Aβ protofibril comprising an Aβ40Arc peptide (SEQ ID NO:1).

10. The method of claim 5, said method comprising administering a purified humanized antibody or fragment thereof that binds a soluble Aβ protofibril comprising an Aβ40Arc peptide (SEQ ID NO:1).

11. The method of claim 6, wherein said composition comprises a purified monoclonal antibody or fragment thereof that binds a soluble Aβ protofibril comprising an Aβ40Arc peptide (SEQ ID NO:1).

12. The method of claim 6, wherein said composition comprises a purified humanized antibody or fragment thereof that binds a soluble Aβ protofibril comprising an Aβ40Arc peptide (SEQ ID NO:1).

* * * * *

SEQUENCE LISTING

```
<160> NUMBER OF SEQ ID NOS: 14

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Gly Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 9
<212> TYPE: PRT
<213> ORGANISM: Homo sapiens

<400> SEQUENCE: 2

Lys Leu Val Phe Phe Ala Glu Asp Val
1               5
```

```
<210> SEQ ID NO 3
<211> LENGTH: 24
<212> TYPE: DNA
<213> ORGANISM: Homo sapiens

<400> SEQUENCE: 3
cctcatccaa atgtccccgt catt                                          24

<210> SEQ ID NO 4
<211> LENGTH: 30
<212> TYPE: DNA
<213> ORGANISM: Homo sapiens

<400> SEQUENCE: 4
gcctaattct ctcatagtct taattcccac                                    30

<210> SEQ ID NO 5
<211> LENGTH: 4
<212> TYPE: PRT
<213> ORGANISM: Homo sapiens

<400> SEQUENCE: 5

His His Gln Lys
1

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 42
<212> TYPE: PRT
<213> ORGANISM: Homo sapiens

<400> SEQUENCE: 7

Asp Ala Glu Phe Arg His Asp Ser Gly Tyr Glu Val His His Gln Lys
1               5                   10                  15

Leu Val Phe Phe Gly Glu Asp Val Gly Ser Asn Lys Gly Ala Ile Ile
            20                  25                  30

Gly Leu Met Val Gly Gly Val Val Ile Ala
        35                  40

<210> SEQ ID NO 8
<211> LENGTH: 42
<212> TYPE: PRT
<213> ORGANISM: Homo sapiens

<400> SEQUENCE: 8

Asp Ala Glu Phe Arg His Asp Ser Gly Tyr Glu Val His His Gln Lys
1               5                   10                  15

Leu Val Phe Phe Ala Lys Asp Val Gly Ser Asn Lys Gly Ala Ile Ile
            20                  25                  30

Gly Leu Met Val Gly Gly Val Val Ile Ala
        35                  40
```

-continued

<210> SEQ ID NO 9
<211> LENGTH: 42
<212> TYPE: PRT
<213> ORGANISM: Homo sapiens

<400> SEQUENCE: 9

Asp Ala Glu Phe Arg His Asp Ser Gly Tyr Glu Val His His Gln Lys
1               5                   10                  15

Leu Val Phe Phe Ala Glu Asn Val Gly Ser Asn Lys Gly Ala Ile Ile
            20                  25                  30

Gly Leu Met Val Gly Gly Val Val Ile Ala
        35                  40

<210> SEQ ID NO 10
<211> LENGTH: 42
<212> TYPE: PRT
<213> ORGANISM: Homo sapiens

<400> SEQUENCE: 10

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 11
<211> LENGTH: 140
<212> TYPE: PRT
<213> ORGANISM: Homo sapiens

<400> SEQUENCE: 11

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 12
<211> LENGTH: 140
<212> TYPE: PRT
<213> ORGANISM: Homo sapiens

<400> SEQUENCE: 12

Met Asp Val Phe Met Lys Gly Leu Ser Lys Ala Lys Glu Gly Val Val
1               5                   10                  15

```
Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 13
<211> LENGTH: 140
<212> TYPE: PRT
<213> ORGANISM: Homo sapiens

<400> SEQUENCE: 13

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 14
<211> LENGTH: 140
<212> TYPE: PRT
<213> ORGANISM: Homo sapiens

<400> SEQUENCE: 14

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60
```

```
Asn Val Gly Gly Ala Val Val Thr Gly Val Thr Ala Val Ala Gln Lys
65              70              75              80

Thr Val Glu Gly Ala Gly Ser Ile Ala Ala Ala Thr Gly Phe Val Lys
                85              90              95

Lys Asp Gln Leu Gly Lys Asn Glu Glu Gly Ala Pro Gln Glu Gly Ile
            100             105             110

Leu Glu Asp Met Pro Val Asp Pro Asp Asn Glu Ala Tyr Glu Met Pro
        115             120             125

Ser Glu Glu Gly Tyr Gln Asp Tyr Glu Pro Glu Ala
130             135             140
```